US011517185B2

(12) United States Patent
Hatase et al.

(10) Patent No.: US 11,517,185 B2
(45) Date of Patent: Dec. 6, 2022

(54) ENDOSCOPE

(71) Applicant: PANASONIC I-PRO SENSING SOLUTIONS CO., LTD., Fukuoka (JP)

(72) Inventors: Yuichi Hatase, Fukuoka (JP); Naoyuki Haraguchi, Fukuoka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 136 days.

(21) Appl. No.: 16/982,862

(22) PCT Filed: Apr. 19, 2019

(86) PCT No.: PCT/JP2019/016907
§ 371 (c)(1),
(2) Date: Sep. 21, 2020

(87) PCT Pub. No.: WO2019/208454
PCT Pub. Date: Oct. 31, 2019

(65) Prior Publication Data

US 2021/0052139 A1     Feb. 25, 2021

(30) Foreign Application Priority Data

Apr. 25, 2018   (JP) .............................. JP2018-084435

(51) Int. Cl.
*A61B 1/005*     (2006.01)
*A61B 1/00*      (2006.01)
(Continued)

(52) U.S. Cl.
CPC .......... *A61B 1/0051* (2013.01); *A61B 1/0008* (2013.01); *A61B 1/0058* (2013.01); *A61B 1/05* (2013.01); *A61B 1/313* (2013.01)

(58) Field of Classification Search
CPC ... A61B 1/0008; A61B 1/0051; A61B 1/0057; A61B 1/0058; A61B 1/05
See application file for complete search history.

(56) References Cited

U.S. PATENT DOCUMENTS 3,610,231 A   10/1971  Takahashi et al.
4,776,844 A   10/1988  Ueda
(Continued)

FOREIGN PATENT DOCUMENTS

JP   48-010700 A   3/1973
JP   63-021065 A   1/1988
(Continued)

OTHER PUBLICATIONS

U.S. Appl. No. 16/981,019 to Takashi Kubara et al., filed Sep. 15, 2020.
(Continued)

*Primary Examiner* — Aaron B Fairchild
(74) *Attorney, Agent, or Firm* — Greenblum & Bernstein, P.L.C.

(57) ABSTRACT

An objective is to achieve an endoscope in which a distal part of an insertion unit has a reduced diameter, yet the endoscope has good pushability so that buckling at the distal part can be avoided. This endoscope is provided with: an imaging unit having a lens and an imaging element; a resin tube which extends from the imaging unit to the proximal side opposite the distal side, and through which a cable conductively connected to the imaging element is inserted; and an elastic wire which has a distal end disposed outwardly of the imaging element, is inserted in and extends through the resin tube, and has flexibility and bending stiffness.

5 Claims, 23 Drawing Sheets

(51) Int. Cl.
*A61B 1/05* (2006.01)
*A61B 1/313* (2006.01)

(56) References Cited

U.S. PATENT DOCUMENTS

| | | | |
|---|---|---|---|
| 4,989,586 A * | 2/1991 | Furukawa | A61B 1/05 600/110 |
| 9,848,757 B2 | 12/2017 | Haraguchi et al. | |
| 10,613,314 B2 | 4/2020 | Sueyoshi et al. | |
| 2005/0075538 A1* | 4/2005 | Banik | A61B 1/00071 600/152 |
| 2009/0303619 A1* | 12/2009 | Iwasaki | A61B 1/0008 310/306 |
| 2011/0106055 A1 | 5/2011 | Robertson | |
| 2013/0182091 A1 | 7/2013 | Kohno et al. | |
| 2020/0288948 A1 | 9/2020 | Ogata et al. | |

FOREIGN PATENT DOCUMENTS

| | | |
|---|---|---|
| JP | 2007-181530 A | 7/2007 |
| JP | 2012-200353 A | 10/2012 |
| JP | 5657014 B2 | 1/2015 |

OTHER PUBLICATIONS

Official Communication issued in International Bureau of WIPO Patent Application No. PCT/JP2019/016907, dated Jun. 25, 2019, along with an English translation thereof.

\* cited by examiner

ENDOSCOPE

TECHNICAL FIELD

The present disclosure relates to an endoscope.

BACKGROUND ART

In the related art, an insertion portion disposed on a tip end side of an endoscope has flexibility so that it can be inserted though, for example, a bent body cavity. However, since the insertion portion has flexibility, there is a problem that operation on a proximal side (in other words, base end side) of the insertion portion is not properly transmitted to the tip end side of the insertion portion, the tip end side of the insertion portion has an unfixed direction and unnecessarily bends, and it is difficult to smoothly insert the insertion portion to a target part. Therefore, the endoscope needs to have flexibility capable of bending, and flexural rigidity, namely pushability in order to reduce unnecessary bending (so-called buckling) on the tip end side of the insertion portion as the endoscope is pushed.

Thus, for example, the endoscope disclosed in PTL 1 includes a flexible elongate member having at least one inner cavity and configured to be inserted into a body passage of a patient. The flexible elongate member includes a proximal portion, a distal portion, and a central portion disposed between the proximal portion and the distal portion. The distal portion includes a reinforcing member that is movable between a generally linear configuration and a curved configuration. The reinforcing member has an outer cylinder configuration to be disposed within at least a part of the inner cavity of the flexible elongate member. The reinforcing member is movable along the flexible elongate member to a selected place and modifies flexibility of the selected place of the flexible elongate member. The reinforcing member includes a first portion and a second portion. The first portion has first toughness. The second portion has second toughness that is different from the first toughness.

CITATION LIST

Patent Literature

[PTL 1]: Japanese Patent No. 5657014

SUMMARY OF INVENTION

Technical Problem

The endoscope of PTL 1 can move the reinforcing member along a length of the flexible elongate member to the selected place to modify the flexibility of the selected portion or section of the flexible elongate member (for example, to be reinforced or more rigid). However, since the tubular reinforcing member is coaxially inserted through the inside of the tubular flexible elongate member, it is not suitable for reduction in diameter. That is, if the tubular reinforcing member is inserted through the inside of the tubular flexible elongate member, inner space of the flexible elongate member is reduced correspondingly, and disposition space of an imaging unit or the like cannot be secured. Conversely, if accommodation space of an imaging unit or the like is secured in the inner space of the tubular reinforcing member, an outer diameter of the flexible elongate member increases.

The present disclosure has been made in view of the above-described circumstances in the related art, and an object thereof is to provide an endoscope capable of achieving both pushability for reducing buckling of the tip end side of the insertion portion and reduction in diameter of the tip end side of the insertion portion.

Solution to Problem

The present disclosure provides an endoscope including an imaging unit having a lens and an imaging element, a resin tube extending from the imaging unit to a base end side opposite to a tip end side, inserting a cable conductively connected to the imaging element inside, and an elastic wire having flexibility and flexural rigidity with a tip end disposed outside the imaging element, being inserted through the resin tube and extending along the resin tube.

Advantageous Effects of Invention

In the endoscope according to the present disclosure, it is possible to achieve both pushability and reduction in diameter.

DESCRIPTION OF EMBODIMENTS

Hereinafter, each embodiment that specifically discloses an endoscope according to the present disclosure will be described in detail with reference to the accompanying drawings as appropriate. However, detailed description more than necessary may be omitted. For example, detailed description of an already well-known matter or repeated description of substantially the same component may be omitted. This is to avoid unnecessary redundancy of the following description and to facilitate understanding of those skilled in the art. The accompanying drawings and the following description are provided to thoroughly understand the present disclosure by those skilled in the art, and are not intended to limit the subject described in claims.

First Embodiment

Figure 1:
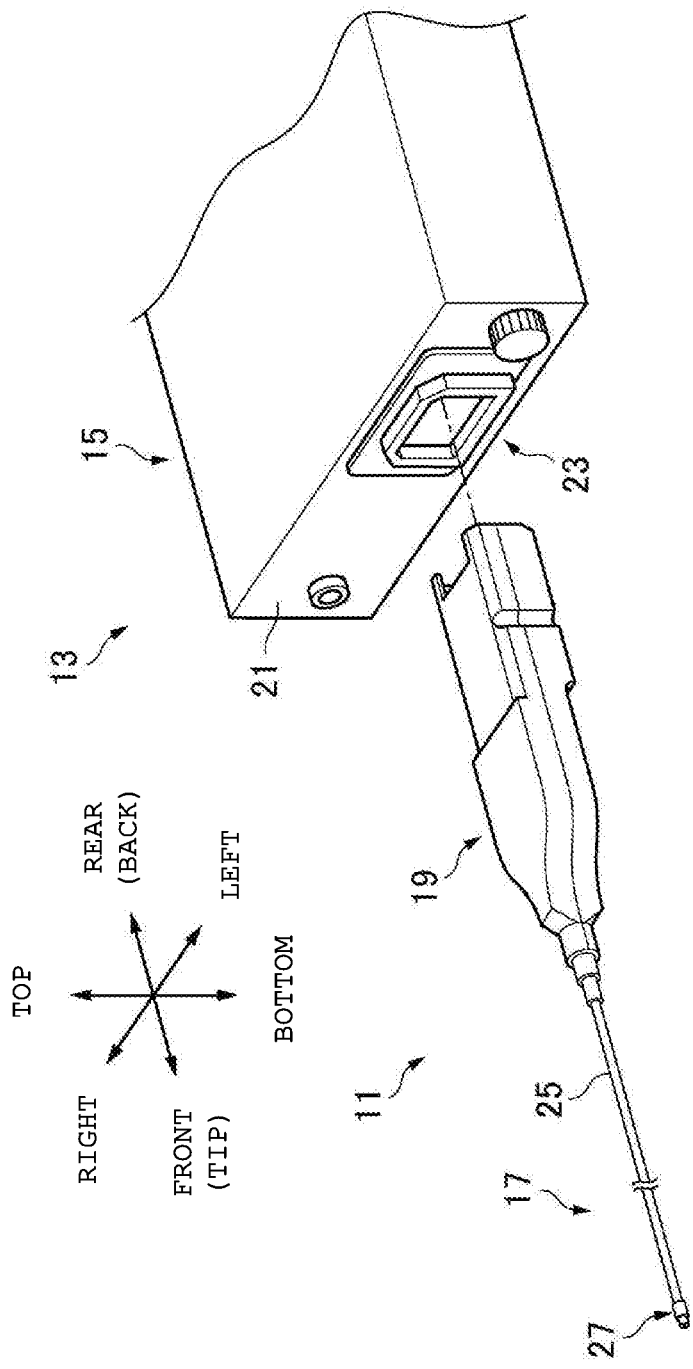
FIG. 1 is an overall configuration diagram showing an example of an endoscope system using an endoscope according to a first embodiment.

FIG. 1 is an overall configuration diagram showing an example of an endoscope system 13 using an endoscope 11 according to a first embodiment. FIG. 1 shows a perspective view of an overall configuration of the endoscope system 13 including the endoscope 11 and a video processor 15. Also, directions used in description of each embodiment are based on directions in FIG. 1, and when directions are described in other drawings, the directions follow the directions in FIG. 1. Here, "top" and "bottom" respectively correspond to the upper and lower of the video processor 15 placed on a horizontal plane, and "front (tip)" and "rear (back)" respectively correspond to a tip end side of an insertion portion 17 of the endoscope 11 and a base end side of a plug 19.

As shown in FIG. 1, the endoscope system 13 includes, for example, an endoscope 11 that is a medical flexible scope and the video processor 15 that performs well-known image processing or the like on a still image or a moving image obtained by imaging the inside of an observation object (for example, a blood vessel of a human body) as an example of an object to be examined. The endoscope 11 includes the insertion portion 17 extending substantially in a front-rear direction and inserted into the observation object and the plug 19 to which a rear portion of the insertion portion 17 is connected.

The video processor 15 has a socket 23 that opens in a front wall 21. A rear portion of the plug 19 of the endoscope 11 is inserted into the socket 23. Accordingly, the endoscope 11 can send and receive electric power and various signals (reflection signals, control signals, and the like) to and from the video processor 15.

The insertion portion 17 includes a flexible portion 25 having flexibility with a rear end connected to the plug 19 and a tip end portion 27 connected to a tip end of the flexible portion 25. The flexible portion 25 has an appropriate length corresponding to a method such as various endoscopies or endoscopic operations, and an outer periphery of the flexible portion 25 is covered with, for example, a resin tube 29. The flexible portion 25 connects the tip end portion 27 and the plug 19.

The electric power and various signals are transmitted from the plug 19 to the flexible portion 25 via a cable 31 (see FIG. 5) inserted through the inside of the flexible portion 25. Image data imaged by an imaging element 33 provided on the tip end portion 27 is transmitted from the plug 19 to the video processor 15 via the cable 31. The video processor 15 performs commonly known image processing such as color correction and tone correction on the image data transmitted from the plug 19, and outputs image data after the image processing to a display device (not shown). The display device is, for example, a monitor device having a display device such as a liquid crystal display panel, and displays an image of a subject imaged by the endoscope 11 (for example, data of a still image or a moving image indicating a state in a blood vessel of a person that is a subject).

Since the endoscope 11 is formed with a small diameter, the endoscope 11 can be inserted into a body cavity having a small diameter. The body cavity having a small diameter is not limited to a blood vessel of a human body, and includes a ureter, a pancreatic duct, a bile duct, a bronchiole, and the like. The endoscope 11 can be used for observation of a lesion in the object to be examined (for example, a blood vessel) as, for example, a medical application. The endoscope 11 is also effective at the time of identifying atherosclerotic plaque. The present invention can also be applied to observation by the endoscope 11 at the time of heart catheter examination. Furthermore, the endoscope 11 is also effective to detect a thrombus or atherosclerotic plaque. In the atherosclerotic lesion, a color tone (white, light yellow, yellow) and a surface (smooth, irregular) are observed. In the thrombus, a color tone (red, white, dark red, yellow, brown, mixed color) is observed.

In addition, the endoscope 11 can be used for diagnosis or treatment of renal pelvis or ureteral cancer and idiopathic renal hemorrhage. In this case, the endoscope 11 can be inserted into a bladder from a urethra and can further advance into the ureter to observe the inside of the ureter and a renal pelvis.

In addition, the endoscope 11 can be inserted into a Vater papilla opening in a duodenum. Bile is produced from the liver and goes through a bile duct, and pancreatic juice is produced from a pancreas, goes through the pancreatic duct, and discharged from the Vater papilla of the duodenum. The endoscope 11 can be inserted from the Vater papilla that is an opening portion of the bile duct and the pancreatic duct to enable observation of a bile duct or a pancreatic duct.

Further, the endoscope 11 can be inserted into a bronchial tube. The endoscope 11 is inserted from an oral cavity or a nasal cavity of a specimen (namely patient) in a supine position. The endoscope 11 is inserted into a trachea through a pharynx and a larynx while visually recognizing vocal cords. The bronchial tube becomes thinner each time it branches. For example, according to the endoscope 11 having a maximum outer diameter of less than 2 mm, the lumen can be confirmed up to a subsegment bronchial tube.

Figure 2:
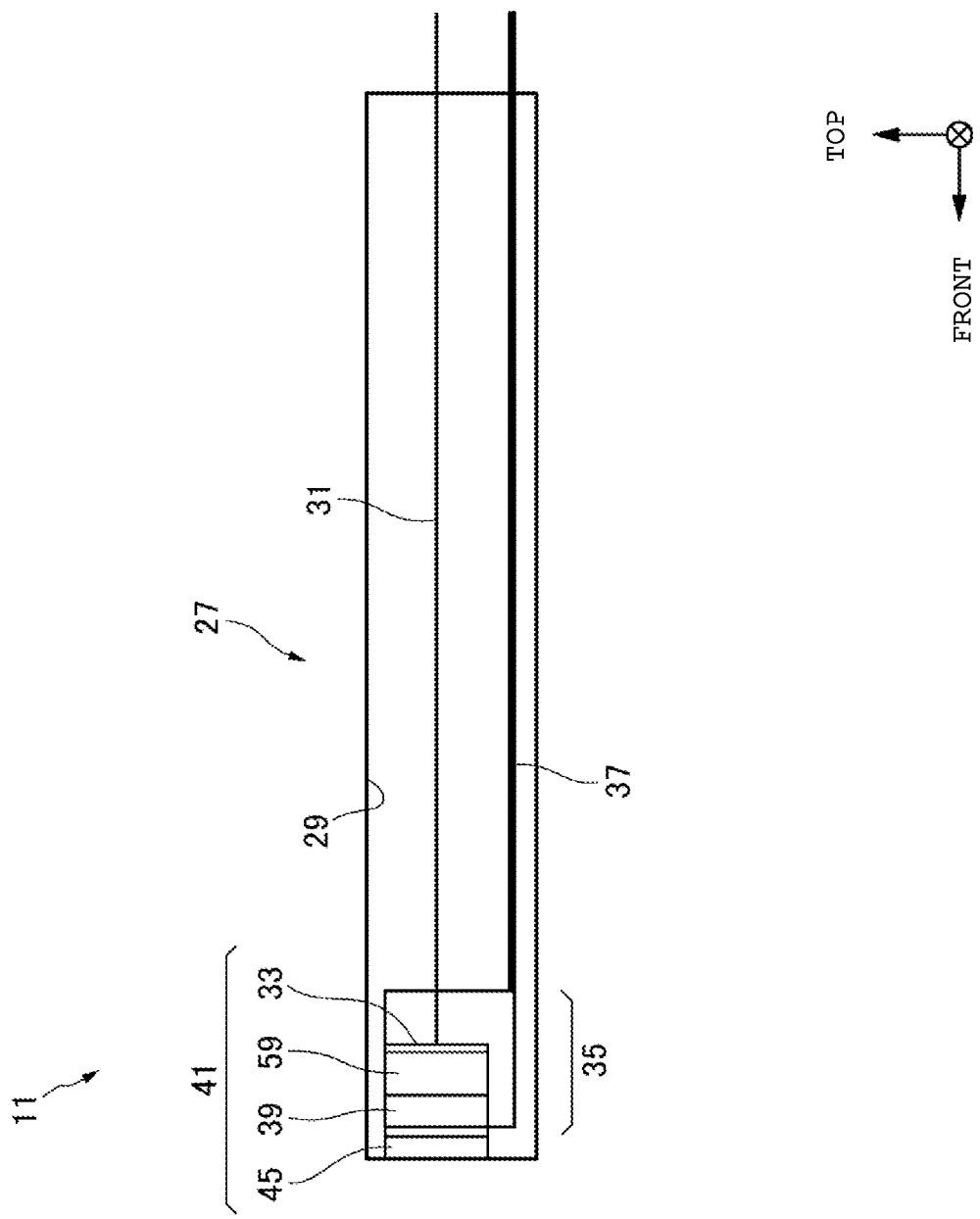
FIG. 2 is a schematic view schematically illustrating a main part of the endoscope according to the first embodiment.

FIG. 2 is a schematic view schematically illustrating a main part of the endoscope 11 according to the first embodiment. The endoscope 11 includes a tip end holder 35, a resin tube 29, and an elastic wire 37 as main components. The tip end holder 35 houses an imaging unit 41 having a quadrangular lens 39 and an imaging element 33.

Figure 3:
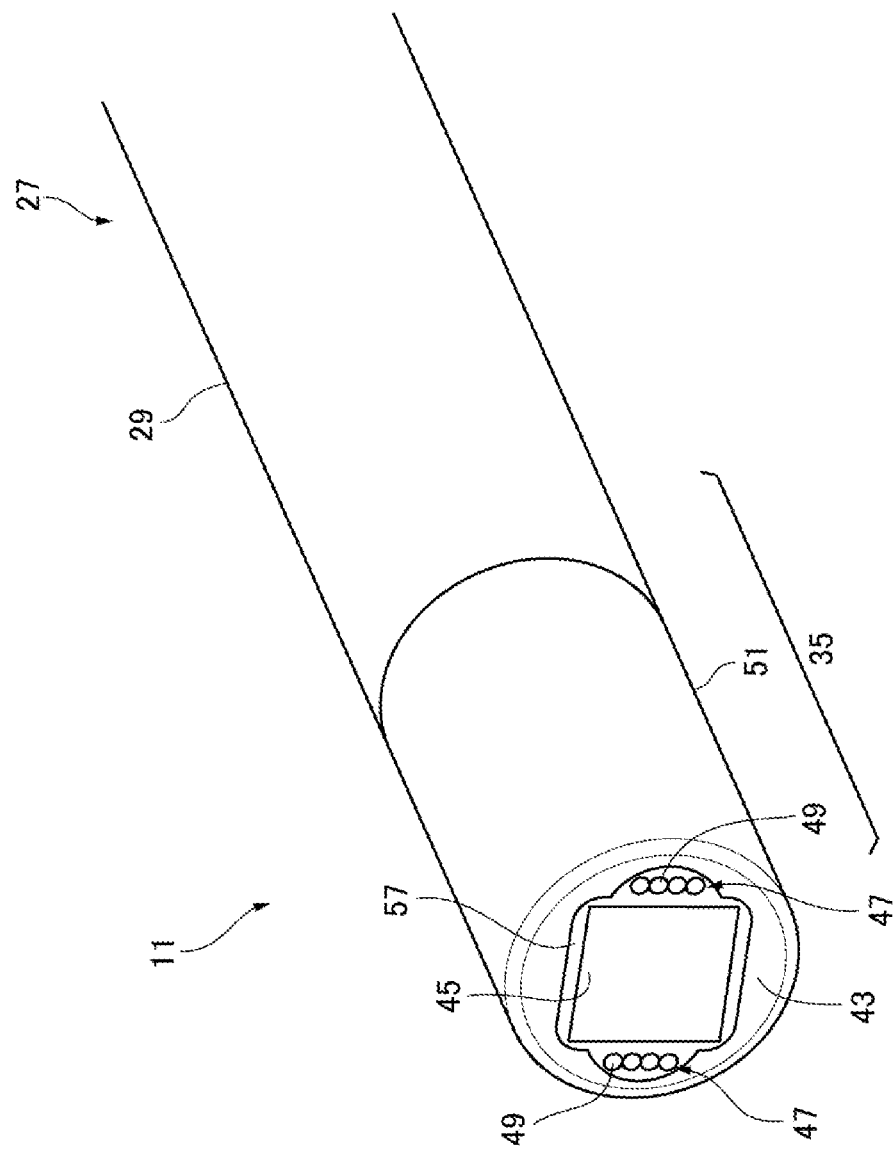
FIG. 3 is a perspective view of a tip end portion of the endoscope according to the first embodiment.

FIG. 3 is a perspective view of the tip end portion 27 of the endoscope 11 according to the first embodiment. The tip end holder 35 is formed in a circular outer shape. In the tip end holder 35, light from the subject (that is, reflected light) is incident on the imaging element 33 through the lens 39 from a tip end surface 43. The resin tube 29 extends from a side opposite to the tip end surface 43 of the tip end holder 35, through whose inside the cable 31 (see FIG. 2) conductively connected to the imaging element 33 is inserted. A rear end of the cable 31 is connected to the plug 19. Further, the tip end holder 35 serves as a light shielding member that blocks incidence of unnecessary light (for example, light from a side surface), and serves as a holder for fixing optical fibers 49 and disposing the elastic wire 37.

Figure 4:
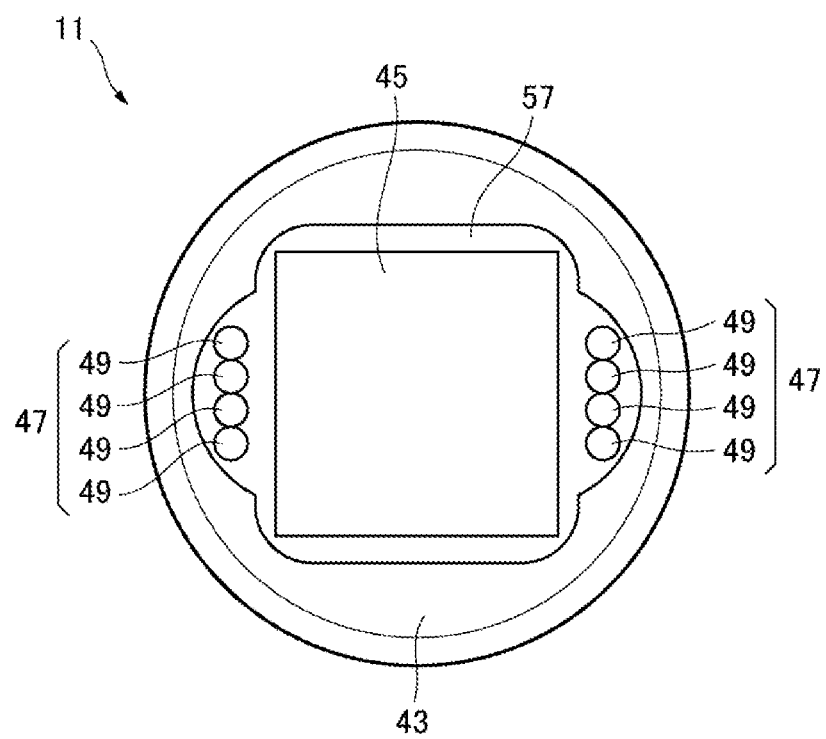
FIG. 4 is a front view of the endoscope shown in FIG. 3.

FIG. 4 is a front view of the endoscope 11 shown in FIG. 3. A quadrangular objective cover glass 45 is provided in a central portion of the tip end surface 43. The objective cover glass 45 is disposed in front of the lens 39 of the imaging unit 41. In the tip end surface 43, light incident end surfaces of a plurality of (four in an example shown in FIG. 4) optical fibers 49 constituting a pair of light guides 47 are disposed in two lines along a pair of parallel sides of the objective cover glass 45.

Figure 5:
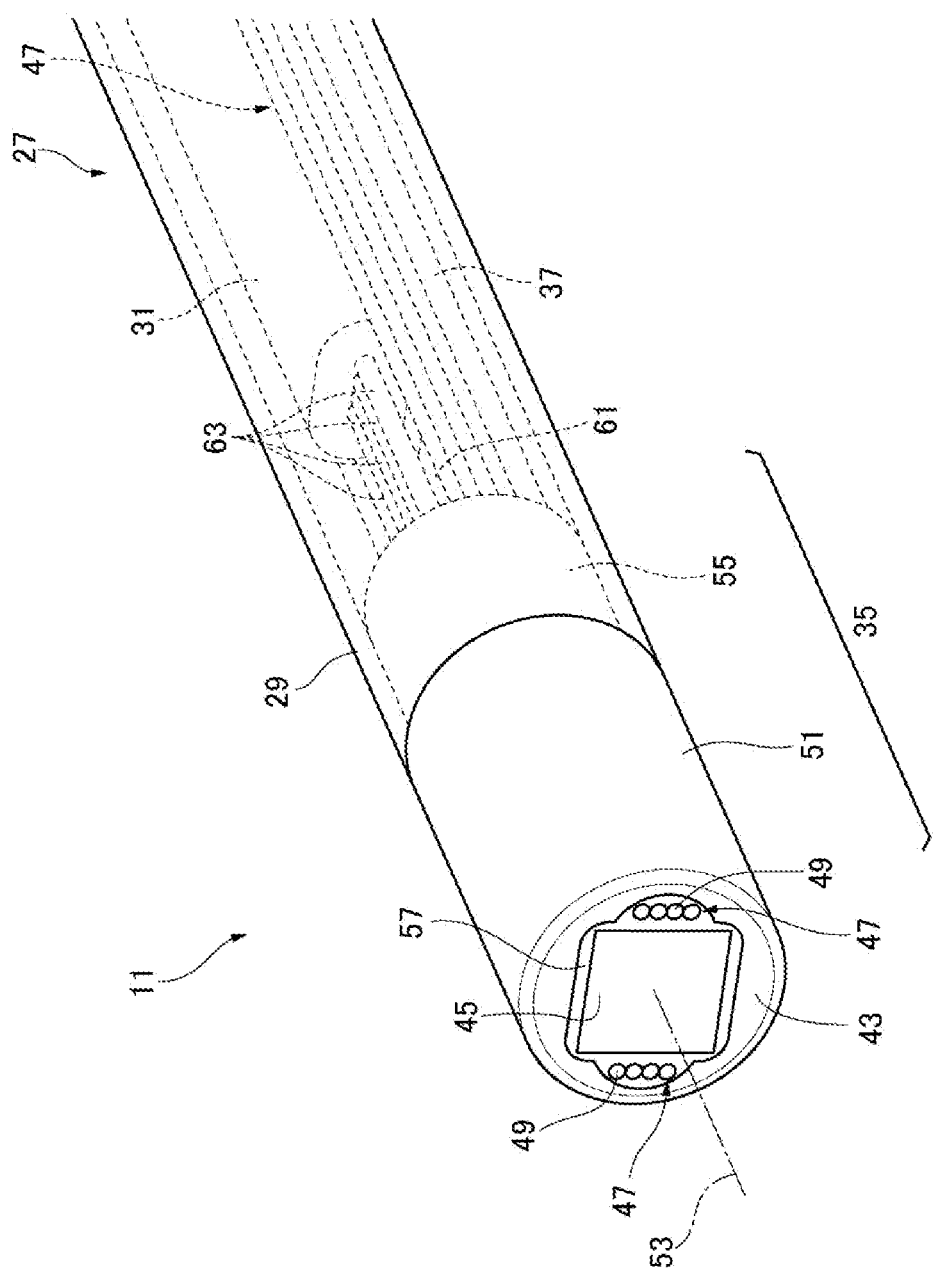
FIG. 5 is a perspective view of the endoscope shown in FIG. 3.

FIG. 5 is a perspective view of the endoscope 11 shown in FIG. 3. In the first embodiment, the tip end holder 35 has a bottomed cylindrical portion 51. The bottomed cylindrical portion 51 is formed in a cylindrical shape having a tip end surface 43 at one end in an extending direction of an axis 53. That is, the tip end surface 43 constitutes a part of a bottom surface (end surface) of the bottomed cylindrical portion 51. The bottomed cylindrical portion 51 has a mounting tube 55 connected to a rear portion. The mounting tube 55 is fixed to an inner circumference of the rear portion of the bottomed cylindrical portion 51 by welding or brazing, and is led out from a rear end of the bottomed cylindrical portion 51. The bottomed cylindrical portion 51 and the mounting tube 55 are formed of, for example, stainless steel, and are integrally joined by a forming process such as machining. The resin tube 29 having the same outer diameter as the bottomed cylindrical portion 51 is fixed on an outer circumference of the mounting tube 55.

Figure 6:
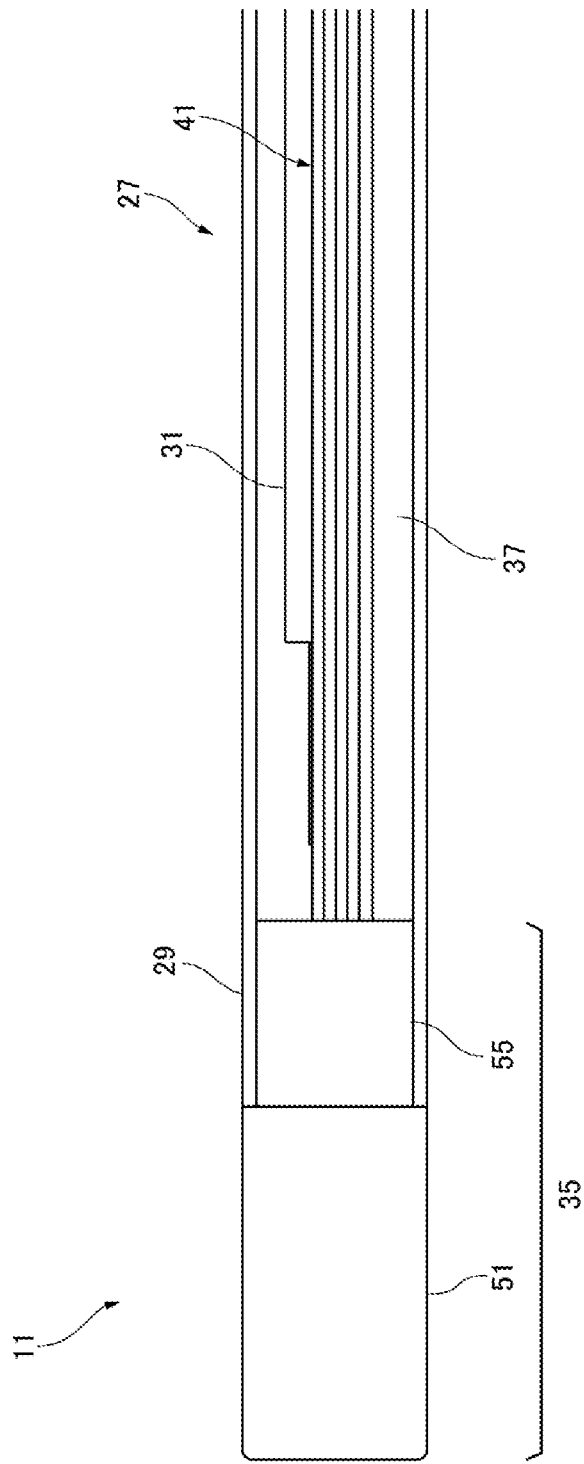
FIG. 6 is a side view of the endoscope shown in FIG. 5.

FIG. 6 is a side view of the endoscope 11 shown in FIG. 5. In the endoscope 11, a tip end of the elastic wire 37 is conductively connected to the bottomed cylindrical portion 51. One elastic wire 37 is inserted through the inside of the resin tube 29. The elastic wire 37 is disposed below a side opposite to the upper cable 31 by sandwiching the light guide 47. An insertion position of the elastic wire 37 is not limited to this. As will be described later, the elastic wire 37 may be disposed in any space as long as it is outside the imaging element 33.

Figure 7:
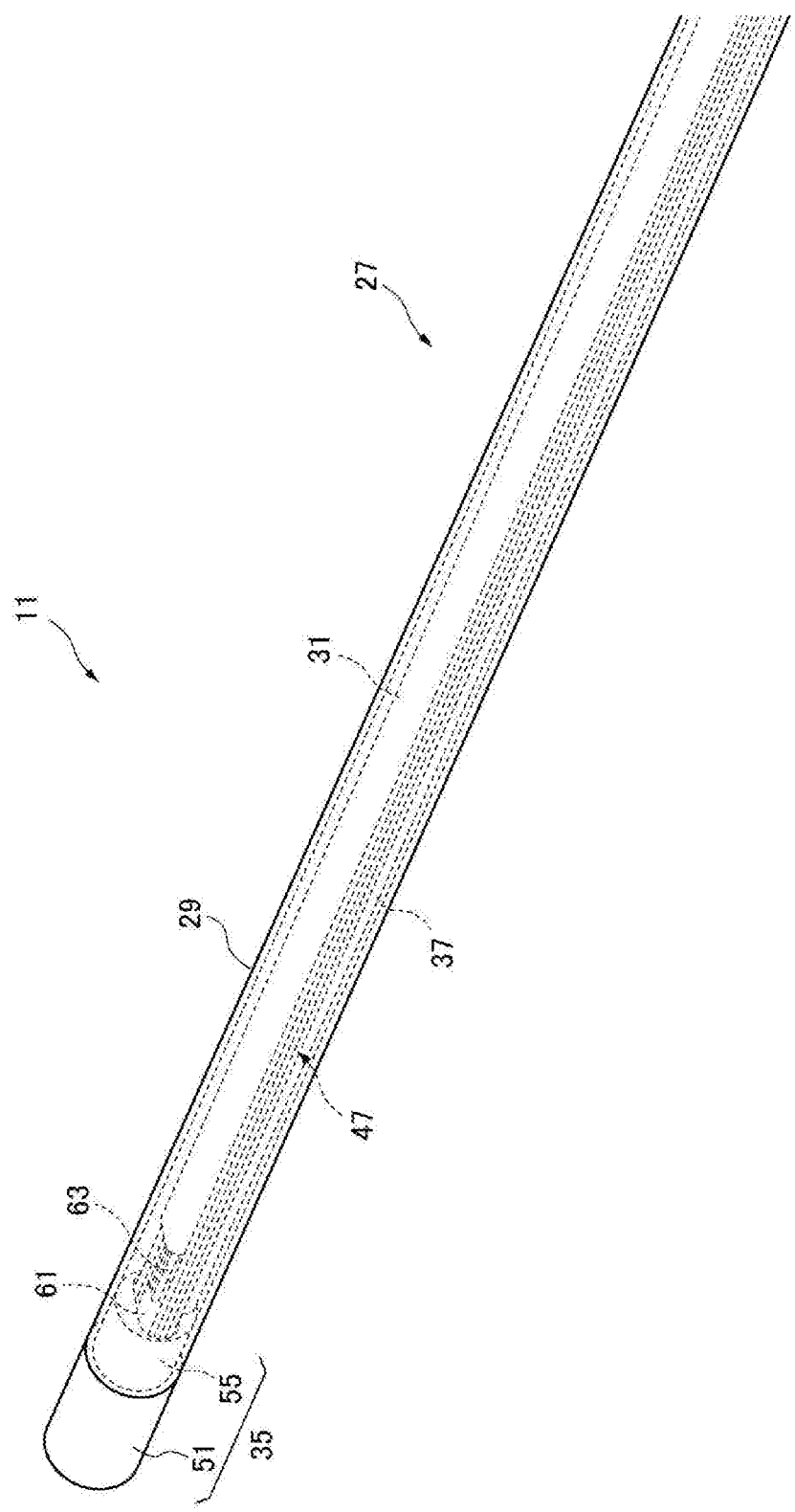
FIG. 7 is a perspective view seen from oblique rear of the endoscope shown in FIG. 5.

FIG. 7 is a perspective view seen from an oblique rear of the endoscope 11 shown in FIG. 5. The elastic wire 37 is inserted through the inside of the resin tube 29 and extends to a side opposite to the tip end holder 35. The elastic wire 37 extends to the proximal side of the endoscope 11. Preferably, a rear end of the elastic wire 37 is fixed to the plug 19 through the inside of the resin tube 29. The elastic wire 37 has flexibility and has predetermined flexural rigidity.

Here, the elastic wire 37 can be an example of a column subjected to compression. It can be considered that the column subjected to compression is divided into a short column and a long column. In the short column, a length of a straight column is shorter than a sectional dimension. The short column shrinks straight due to an axial compression load and breaks when compressive stress exceeds compressive strength of the material. On the other hand, a length of the long column is much longer than the sectional dimension. When the axial compression load reaches a certain magnitude, the long column that has been shrunk straight until now rapidly begins to bend largely toward the side. This phenomenon is referred to as buckling. The load is referred to as a buckling load. The buckling load is a value related to flexural rigidity of a column rather than strength of a material.

The flexural rigidity is an index indicating difficulty in flexural deformation of the column, and is expressed by a product of a second moment of area I and a Young's modulus E of the material. The second moment of area I is, for example, $I=(\pi/64)d^4$ in a circular section having a diameter d.

Buckling of the column depends on a length L of the column, a condition coefficient n of a terminal, and the flexural rigidity EI. In the long column having buckling stress equal to or less than a proportional limit, a buckling load Pk is determined by the following Euler formula (Formula 1).
(Formula 1)

$$Pk=n\pi^2 EI/L^2 \qquad (1)$$

Wherein in the (Formula 1), n is a coefficient according to conditions of the terminal, and n=0.25 if one end is fixed and the other end is a free end.

Regarding the flexural rigidity, the following (Formula 2) can be derived from the (Formula 1).
(Formula 2)

$$EI=PkL^2/n\pi^2 \qquad (2)$$

The endoscope 11 includes, as a constituent member, the elastic wire 37 having flexural rigidity EI capable of transmitting an axial force due to an operation force on the proximal side to the tip end holder 35.

As a material of the elastic wire 37, for example, a shape memory alloy (for example, Ni—Ti: nickel titanium) can be used. In addition, a stainless steel wire may be used for the elastic wire 37. An outer diameter of the elastic wire 37 can beset to, for example, 0.1 mm to 0.4 mm.

Figure 8:
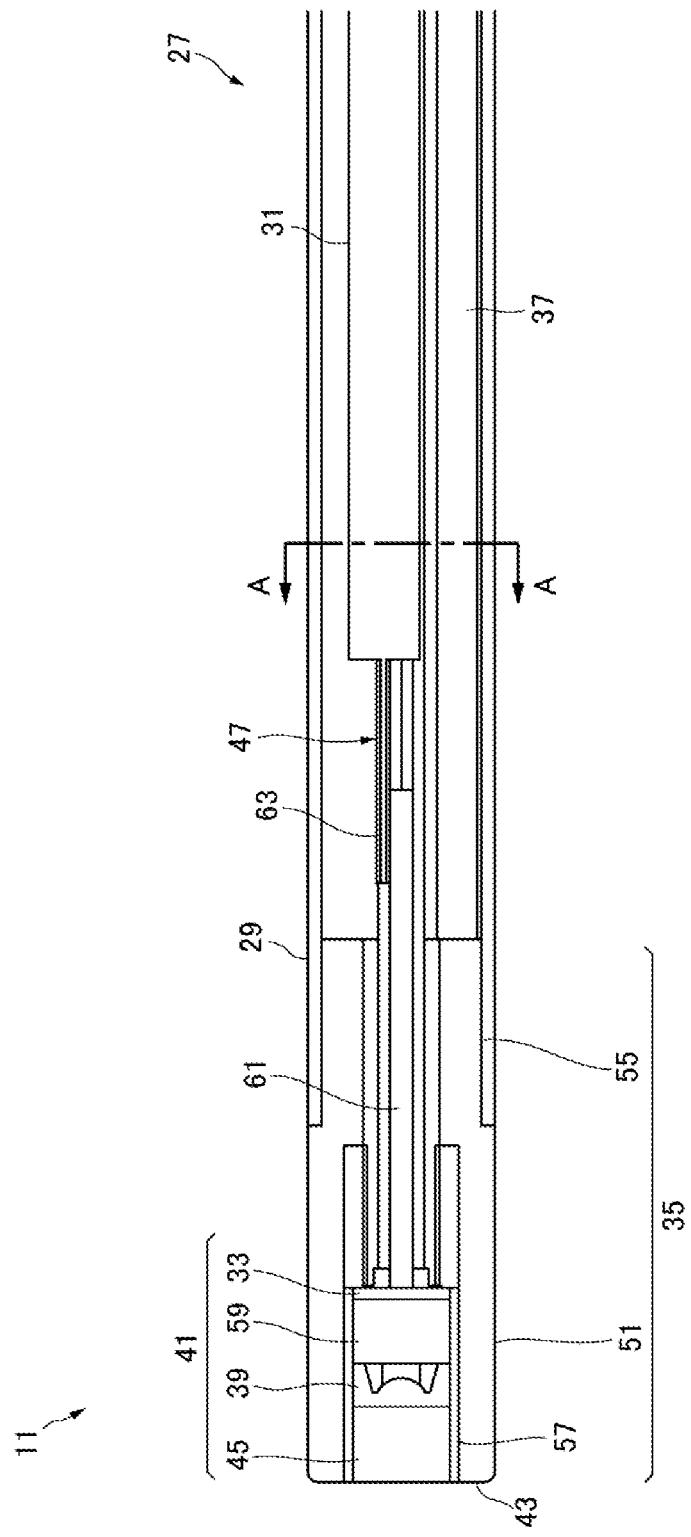
FIG. 8 is a side sectional view of the endoscope shown in FIG. 5.

FIG. 8 is a side sectional view of the endoscope 11 shown in FIG. 5. A lens barrel 57 is fixed to a central portion of the tip end surface 43 in the bottomed cylindrical portion 51. The lens barrel 57 is formed in a square cylindrical shape surrounding the rectangular objective cover glass 45. The objective cover glass 45 exposed to the tip end surface 43 is fixed to the tip end of the lens barrel 57. The lens 39 is fixed to a back surface of the objective cover glass 45. An element cover glass 59 is fixed to the back surface of the lens 39.

A quadrangular imaging element 33 is fixed to a back surface of the element cover glass 59. The objective cover glass 45, the lens 39, the element cover glass 59, and the imaging element 33 constitute an imaging unit 41. In the imaging unit 41, a substrate is vertically connected to a back surface of the imaging element 33.

In the substrate, a plurality of (for example, four in the first embodiment) linear conductors are disposed in parallel on the same plane, and the conductors are molded into an insulating coated plate shape. The substrate is formed in a quadrangle whose one end and the other end sides in an extending direction of the conductor are shorter than one side of the imaging element 33. The conductor at one end and the other end of the substrate is exposed on at least one of front and back of a plate surface.

The substrate has, for example, flexibility. As the substrate, a flexible printed wiring substrate (FPC) or the like obtained by pattern printing a conductor on an insulating substrate having flexibility can be used.

Further, in the substrate, a conductor may be insulating coated, and a conductor may be printed on the insulating substrate. As the substrate, the flexible printed wiring substrate (FPC) having flexibility, a laminated substrate obtained by pattern printing the conductor on the insulating substrate, or the like can be used. In the present embodiment, a flexible wiring substrate 61, which is the FPC having flexibility, is used as the substrate.

An electrical component (not shown) that conducts power with the conductor may be mounted on the flexible wiring substrate 61. Examples of the electrical component include a bypass condenser that is effective in reducing noise or the like. A land for mounting the electrical component is formed on the flexible wiring substrate 61. The land is connected to a conductor of the flexible wiring substrate 61.

A plurality of (for example, four) core wires 63 of the cable 31 are connected to the exposed conductor separately at the other end of the flexible wiring substrate 61. In the cable 31, a plurality of core wires 63 are disposed on the same plane and are collectively insulating coated. As the cable 31, for example, a ribbon shape cable can be used.

In the cable 31, the core wires 63 each are covered with an internal coating. The plurality of core wires 63 covered with the inner coating and insulated separately are collectively covered with a shield from the outside of the inner coating and formed in a strip shape.

Figure 9:
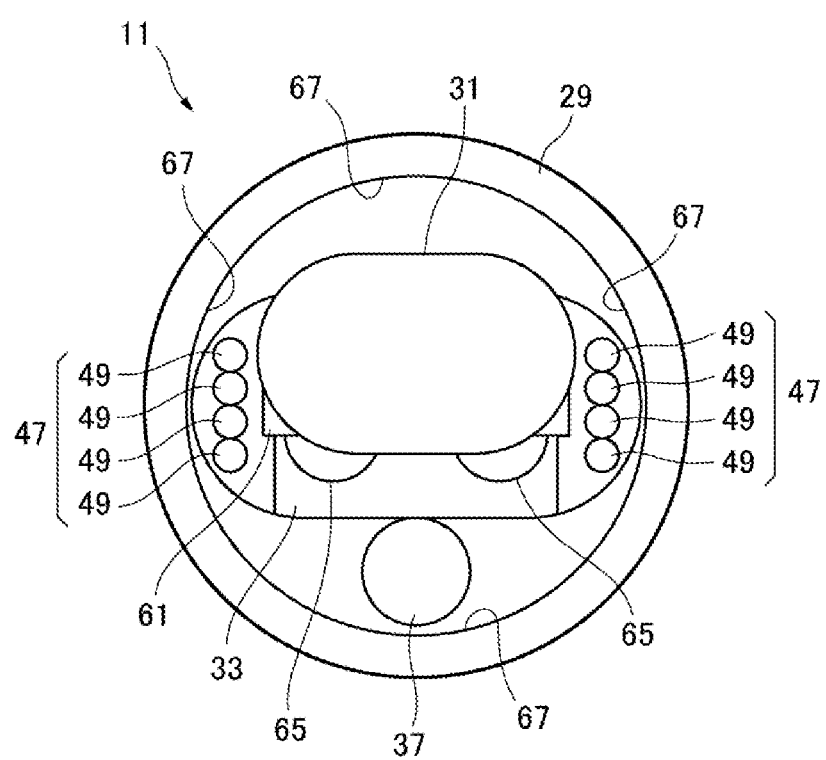
FIG. 9 is a sectional view taken along A-A of FIG. 8.

FIG. 9 is a sectional view taken along A-A of FIG. 8. The imaging element 33 is formed in, for example, a quadrangle having one side of 1 mm or less. In a case of the endoscope 11 having a contour of 1 mm, the imaging element 33 is formed with a side of about 0.5 mm. A plurality of (for example, four) pads 65 are provided on a back surface opposite to an imaging surface of the imaging element 33. Each conductor of the flexible wiring substrate 61 is conductively fixed to each of the pads 65 by brazing, laser welding, or the like. As a result, the flexible wiring substrate 61 is vertically connected to the imaging element 33. The cable 31 is connected to the rear side of the flexible wiring substrate 61.

Figure 10:
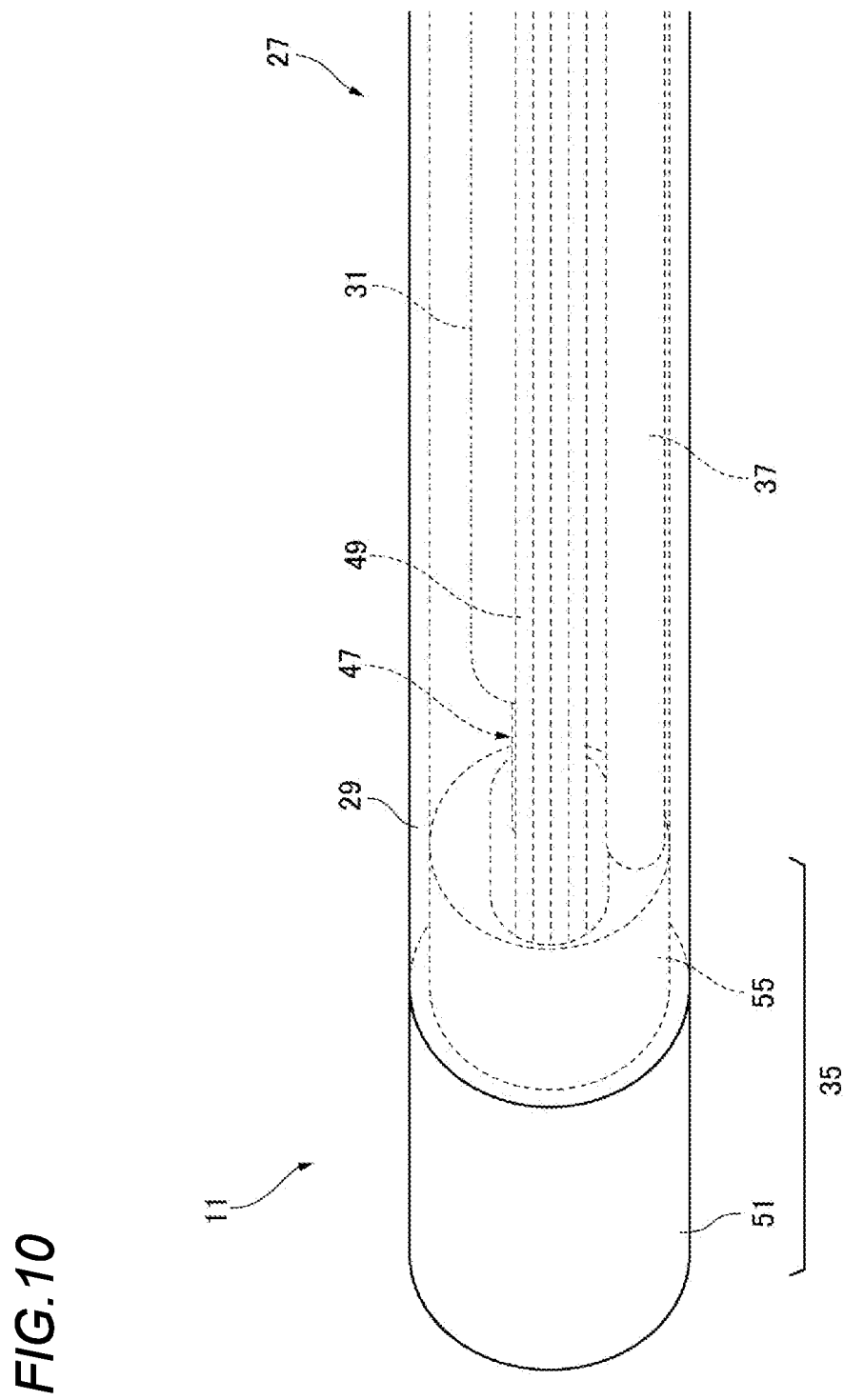
FIG. 10 is a perspective view of a tip end portion illustrating a joint between a bottomed cylindrical portion and an elastic wire.

FIG. 10 is a perspective view of the tip end portion 27 illustrating a joint between the bottomed cylindrical portion 51 and the elastic wire 37. The tip end of the elastic wire 37 is disposed on the bottomed cylindrical portion 51 outside the imaging element 33. In the first embodiment, the tip end of the elastic wire 37 is disposed on a rear end surface of the mounting tube 55. The tip end of the elastic wire 37 can be fixed to the mounting tube 55 by, for example, a binding material, brazing, or welding. A fixing portion of the elastic wire 37 is not limited to the rear end surface of the mounting tube 55. The fixing portion of the elastic wire 37 may be any part of the bottomed cylindrical portion 51 as long as it is outside the imaging element 33. The tip end of the elastic wire 37 may be not necessarily fixed to the mounting tube 55. That is, the tip end of the elastic wire 37 may be disposed away from the vicinity of the mounting tube 55. In this case, a separation distance between the elastic wire 37 and the mounting tube 55 may be a distance that does not significantly decrease the flexural rigidity EI that can transmit the axial force due to the operation force on the proximal side to the tip end holder 35.

Figure 11:
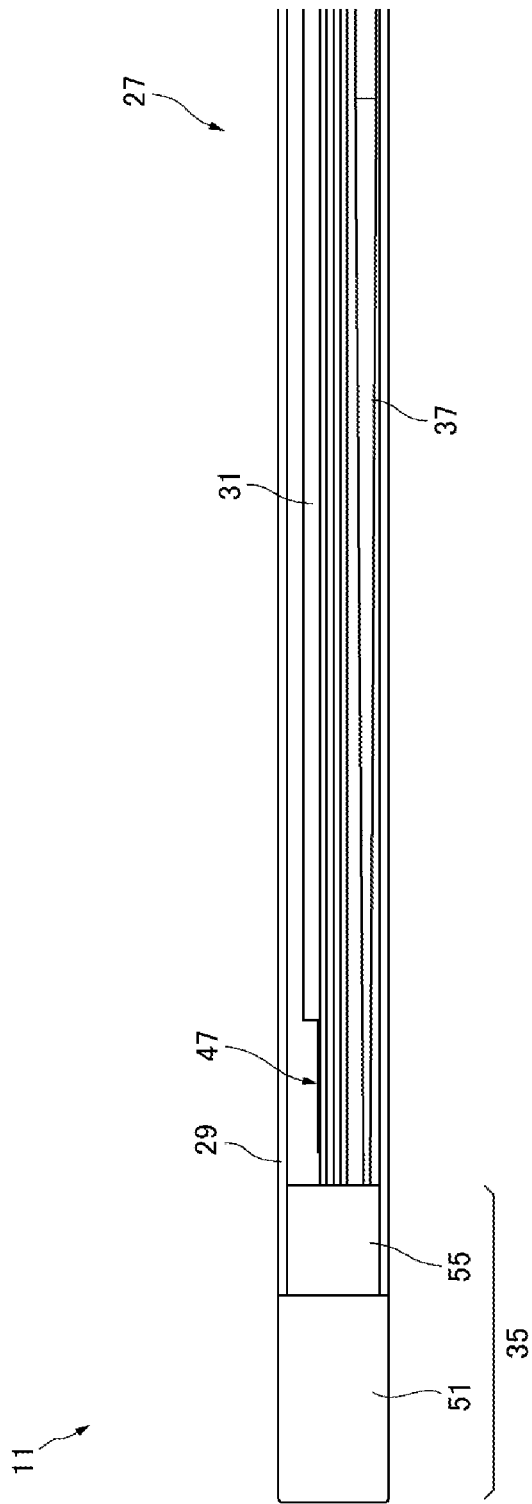
FIG. 11 is a side view of seeing through a part of an endoscope of a modification in which an elastic wire is tapered.

FIG. 11 is a side view of seeing through a part of the endoscope 11 of a modification in which the elastic wire 37 is tapered. The endoscope 11 can be formed such that the flexibility of the elastic wire 37 is different between a tip end side and a base end side. The elastic wire 37 can be formed such that the flexibility is different between the tip end side and the base end side by, for example, changing the material. Further, the elastic wire 37 can be formed such that the flexibility is different between the tip end side and the base end side by changing the outer diameter.

In the first embodiment, the elastic wire 37 is formed such that the flexibility is different between the tip end side and the base end side by changing the outer diameter. That is, as shown in FIG. 11, the elastic wire 37 has a taper shape that is tapered toward the tip end side, so that the tip end side is formed more flexible than the base end side.

Next, working of a configuration of the endoscope 11 according to the first embodiment will be described.

The endoscope 11 according to the first embodiment includes the imaging unit 41 having the lens 39 and the imaging element 33. The endoscope 11 includes a resin tube 29 extending from the imaging unit 41 to the base end side opposite to the tip end side, through whose inside the cable 31 conductively connected to the imaging element 33 is inserted. The endoscope 11 includes the elastic wire 37 having flexibility and flexural rigidity with a tip end disposed outside the imaging element 33, which is inserted through the resin tube 29 and extends.

More specifically, the endoscope 11 according to the first embodiment houses the imaging unit 41 having the quadrangular lens 39 and the imaging element 33 and includes the tip end holder 35 having a circular outer shape that emits imaging light from the tip end surface 43 to the imaging element 33. The endoscope 11 includes the resin tube 29 extending from a side opposite to the tip end surface 43 of the tip end holder 35. The cable 31 conductively connected to the imaging element 33 is inserted inside of the resin tube 29. The endoscope 11 includes the elastic wire 37 having flexibility and predetermined flexural rigidity with a tip end disposed on the tip end holder 35 outside the imaging element 33, which is inserted through the resin tube 29 and extends to a side opposite to the tip end holder 35.

The endoscope 11 further includes the tip end holder 35 that houses the imaging unit 41. The resin tube 29 and the elastic wire 37 are provided by extending to a base end side opposite to the tip end surface 43 of the tip end holder 35 separately.

In the endoscope 11 according to the first embodiment, the outer diameters of the tip end holder 35 and the resin tube 29 are formed to be, for example, 1 mm to 3 mm or less. An entire length from the tip end holder 35 to, for example, the plug 19 on the proximal side is formed to be, for example, about 1.5 m. Meanwhile, if the endoscope 11 has an outer diameter of about 3 mm, it is easy to secure a relatively large sectional area of the resin tube 29 behind the tip end holder 35 or the cable 31 that transmits a power source or a signal. Therefore, in the endoscope 11 having an outer diameter of about 3 mm, pushability to an aorta or the like is easily ensured since predetermined flexural rigidity is obtained.

On the other hand, when insertion into a coronary artery or the like is considered, the outer diameter of the endoscope 11 is desirably 1.4 mm or less. In the case of the endoscope 11 having an outer diameter of 1.4 mm or less, only a small sectional area can be ensured even if the resin tube 29 or the cable 31 behind the tip end holder 35, and the light guide 47 for illumination are added to the endoscope 11. Therefore, in the endoscope 11 having an outer diameter of 1.4 mm or less, the flexural rigidity cannot be sufficiently ensured, and the endoscope 11 is easy to bend during insertion. That is, even if the endoscope 11 is inserted while holding it at the proximal side, the axial force cannot be transmitted to the tip end holder 35 of 1.5 m in front, and good pushability cannot be obtained.

Therefore, in the endoscope 11, the elastic wire 37 whose tip end is disposed on the tip end holder 35 is inserted through the inside of the resin tube 29 and extends to the proximal side. The elastic wire 37 has a predetermined sectional area, and a material is set by a metal or the like having a large elasticity range. That is, the elastic wire 37 has flexibility, is hard to plastically deform, and has a predetermined flexural rigidity.

In the endoscope 11, the tip end of the elastic wire 37 having flexural rigidity is disposed on the tip end holder 35 and is inserted through the resin tube 29 to the proximal side. Therefore, even if the endoscope 11 has a proximal side and is inserted into a blood vessel or the like, a pushing force is transmitted to the tip end holder 35 by the predetermined flexural rigidity. As a result, even if the endoscope 11 has a small outer diameter of 1 mm or less, it is sure to obtain good pushability where buckling is reduced with respect to the tip end holder of 1.5 m in front.

In the endoscope 11, the tip end of the elastic wire 37 is disposed on the tip end holder 35 outside the imaging element 33. The imaging element 33 is formed in a square shape. The tip end holder 35 that houses the imaging element 33 has a circular shape. In a structure in which the imaging element 33 is housed at a maximum size in an inner circumferential circle, four spaces 67 are generated between the square and the inner circumferential circle of the imaging element 33 in a back view. Each side of the square of the imaging element 33 is a chord, and the space 67 is a crescent shape surrounded by the chord and an arc of the tip end holder 35.

In the endoscope 11, the tip end of the elastic wire 37 is disposed in an optional one space 67 among of the four spaces 67. In this way, the elastic wire 37 having a tip end disposed outside the imaging element 33 can be routed along the cable 31, and interference with the cable 31 can be avoided. Since the elastic wire 37 is disposed on the tip end holder outside the imaging element 33, the axial force 12 applied at the time of pushing is not necessary to act on the imaging element 33. As a result, it is possible to prevent destruction of the imaging element 33 due to the axial force at the time of pushing. In this way, in the endoscope 11, the elastic wire 37 is disposed on the tip end holder 35 by effectively using excess space within the limited circular section, and reduction in diameter is realized while increasing a disposition density of the members. That is, the endoscope 11 achieves both pushability and reduction in diameter.

In the endoscope 11, the tip end holder 35 has the bottomed cylindrical portion 51 made of metal that houses the imaging unit 41 therein, and the tip end of the elastic wire 37 is conductively connected to the bottomed cylindrical portion 51.

In the endoscope 11, the tip end holder 35 has a bottomed cylindrical portion 51 made of metal that covers the imaging unit 41. The elastic wire 37 is made of a conductor. The bottomed cylindrical portion 51 can be conductively connected to an arc portion via the elastic wire 37. Accordingly, without using a conductive member such as a dedicated GND line as a countermeasure against static electricity, the imaging unit 41 housed inside the bottomed cylindrical portion 51 can be reliably shielded against static electricity flying from a 360° direction around the axis. As a result, the endoscope 11 can improve operational reliability of the imaging unit 41 while realizing reduction in diameter.

The endoscope 11 is the endoscope 11, and the flexibility of the elastic wire 37 is higher on the tip end side of the elastic wire 37 than that on the base end side of the elastic wire 37.

In the endoscope 11, the tip end side of the elastic wire 37 is formed to have higher flexibility than the base end side of the elastic wire 37. As an example of a configuration that imparts high flexibility to the tip end side of the elastic wire 37, the endoscope 11 can be formed in a tapered shape with the tip end side of the elastic wire 37 in the same material. In addition, as another example of the configuration that imparts high flexibility to the tip end side of the elastic wire 37, the endoscope 11 can be formed by connecting a different material whose flexibility gradually increases toward the tip end side of the elastic wire 37. In the endoscope 11 having such a configuration, while the pushability is ensured, bending followability of the tip end side of the elastic wire 37 at the time of insertion into the bent body cavity can be enhanced, and insertability of a bending portion can be improved.

In the endoscope 11, the elastic wire 37 is formed using a shape memory alloy.

In the endoscope 11, even when deformation occurs in the elastic wire 37 due to insertion into the body cavity or the like, it is possible to return to the original shape without plastic deformation. In this case, the original shape can have an optional shape such as a linear shape or a bent shape.

Figure 12:
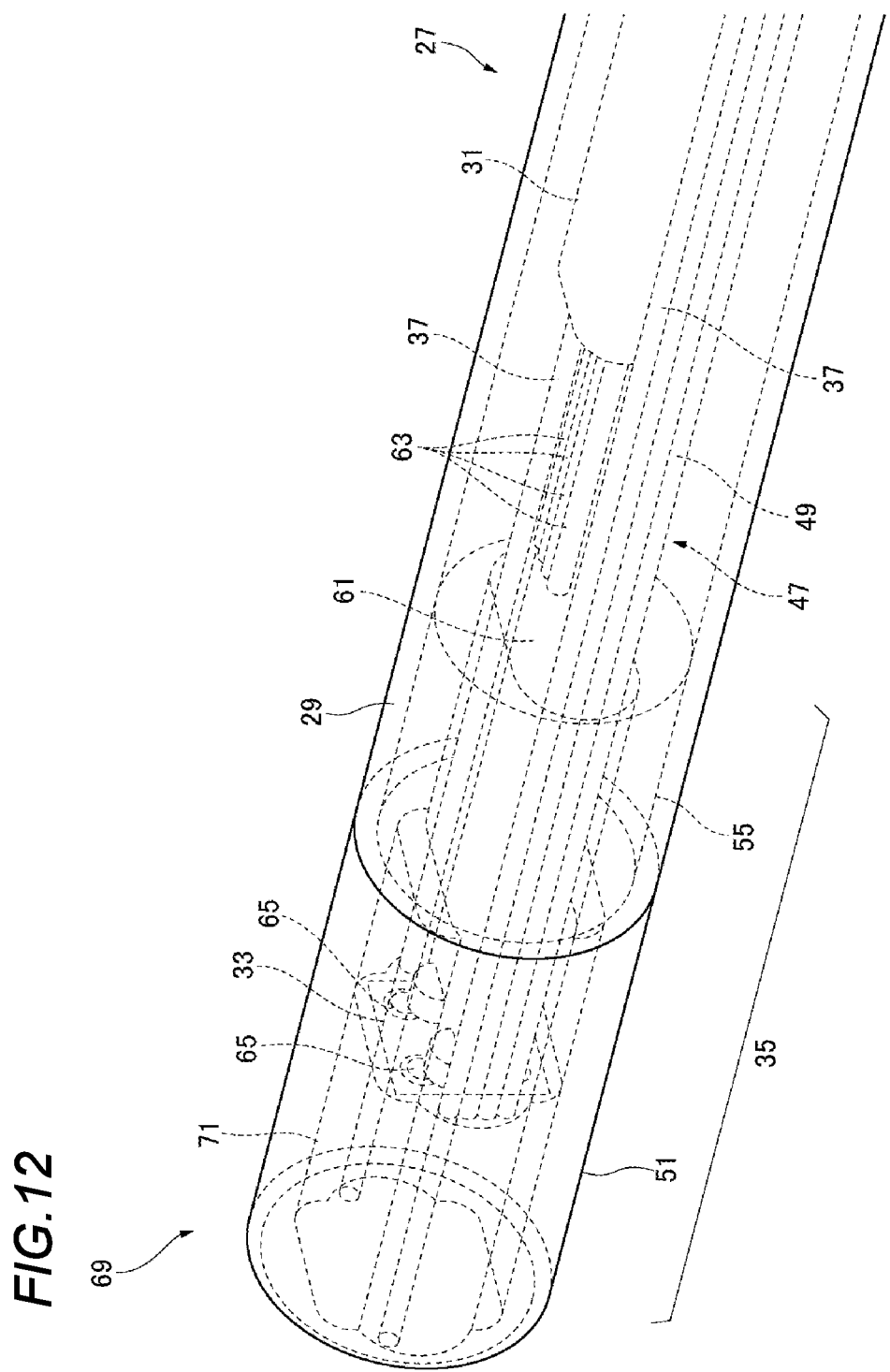
FIG. 12 is a perspective view of the endoscope of the modification in which the elastic wire is provided on a light guide.

FIG. 12 is a perspective view of an endoscope 69 of a modification in which the elastic wire 37 is provided on the light guide 47. In the endoscope 69 of the modification, the elastic wires 37 are one by one passed through an upper stage of a plurality of (each three in the example of FIG. 12) optical fibers 49 constituting a pair of light guides 47. That is, in the endoscope 69, a pair of left and right elastic wires 37 is disposed on the upper stage of each of the light guides 47. The tip end of each elastic wire 37 is embedded and fixed into a binding material 71 together with the optical fiber 49. The binding material 71 is filled in the bottomed cylindrical portion 51.

According to the endoscope 69, since the pair of elastic wires 37 can be disposed to be included in the pair of light guides 47 respectively, it is not necessary to ensure the dedicated space 67 through which the elastic wire 37 is inserted although the number of the light guides 47 is reduced. Therefore, it is possible to further reduce the diameter. In addition, since the pair of left and right elastic wires 37 can be disposed by sandwiching the imaging element 33, the imaging element 33 can be protected more reliably from the flying static electricity compared with a case where one elastic wire 37 is provided.

Second Embodiment

Next, an example of an endoscope 73 according to the second embodiment will be described.

Figure 13:
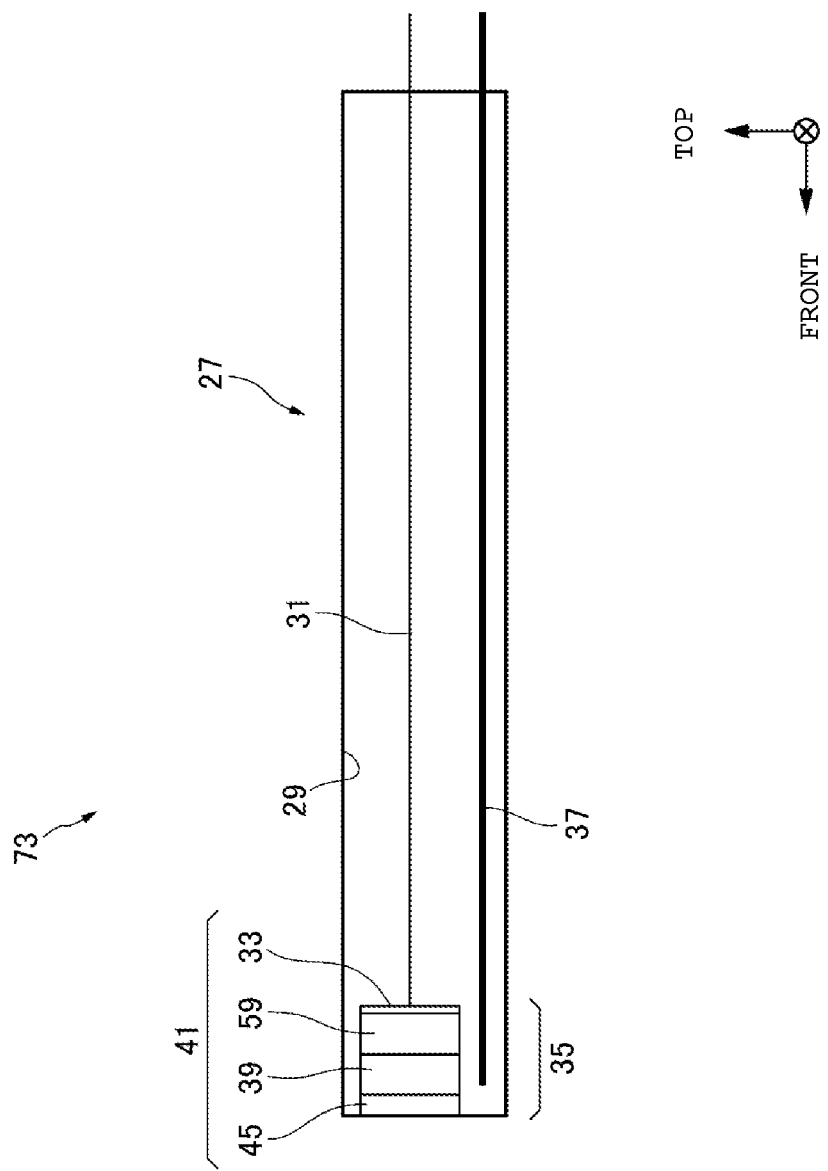
FIG. 13 is a schematic view schematically illustrating a main part of an endoscope according to a second embodiment.

FIG. 13 is a schematic view schematically illustrating a main part of the endoscope 73 according to the second embodiment. In the second embodiment, the same components as the components shown in the first embodiment are denoted by the same reference signs, and repeated description thereof is omitted.

In the endoscope 73 according to the second embodiment, the resin tube 29 extends to the tip end surface 43 of the tip end holder 35. In the endoscope 73, the imaging unit 41 and the tip end of the elastic wire 37 are embedded and disposed in the tip end holder 35.

Figure 14:
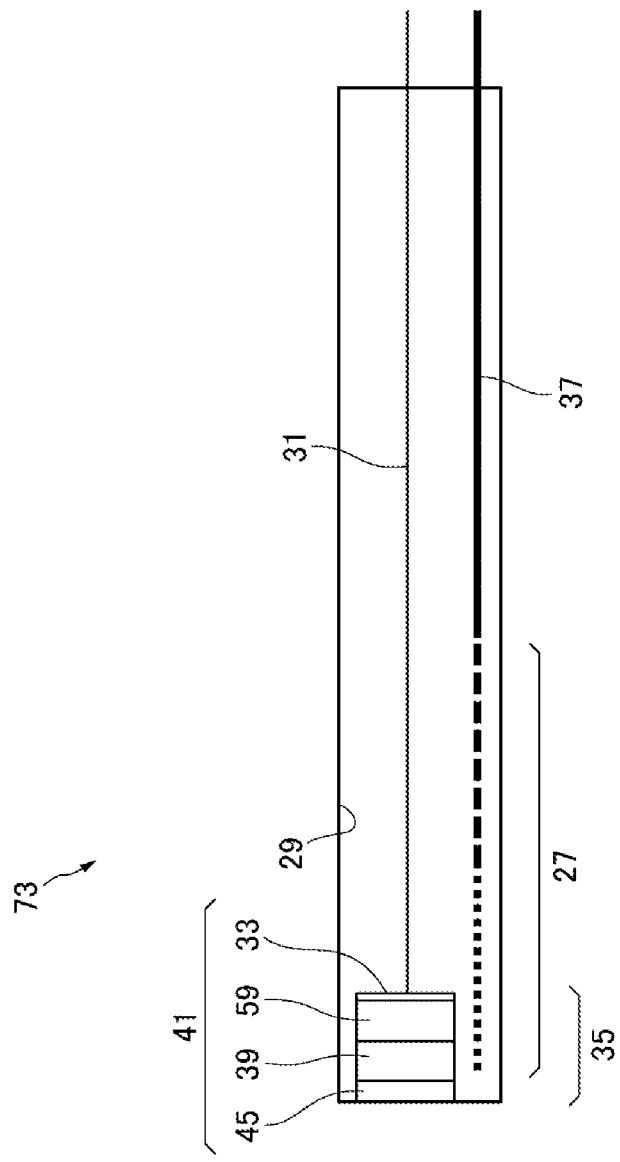
FIG. 14 is a schematic view schematically illustrating a main part of an endoscope of a modification in which an elastic wire is tapered according to the second embodiment.

FIG. 14 is a schematic view schematically illustrating a main part of the endoscope 73 of a modification in which the elastic wire 37 is tapered in the second embodiment. The endoscope 73 is formed such that the flexibility of the elastic wire 37 is different between the tip end side of the elastic wire 37 and the base end side of the elastic wire 37. In the same manner as the first embodiment, the elastic wire 37 has a tapered shape that is tapered toward the tip end side of the elastic wire 37, so that the tip end side of the elastic wire 37 is formed more flexible than the base end side of the elastic wire 37.

Figure 15:
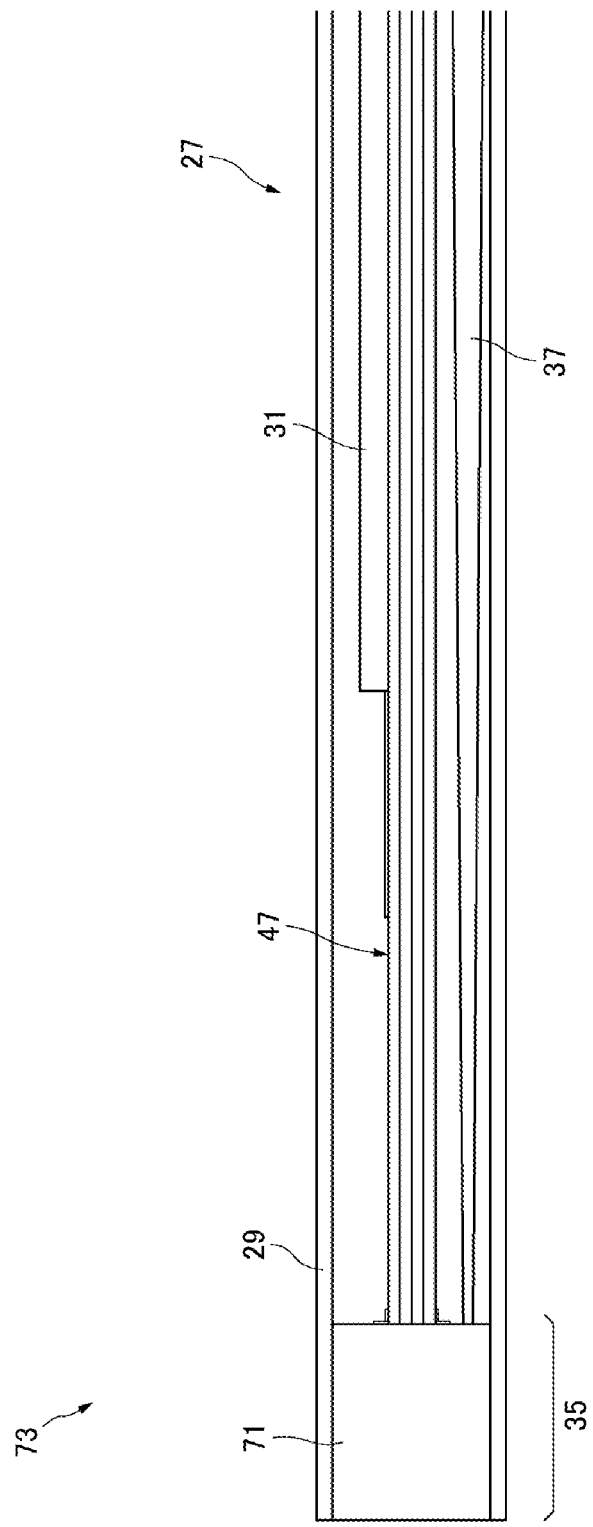
FIG. 15 is a side view of seeing through a part of the endoscope according to the second embodiment.

FIG. 15 is a side view of seeing through a part of the endoscope 73 according to the second embodiment. The endoscope 73 is molded by solidifying the binding material 71 into a cylindrical shape inside the resin tube 29 of the tip end holder 35. The light guide 47 and the elastic wire 37 are led out from the back end surface of the solidified binding material 71.

Figure 16:
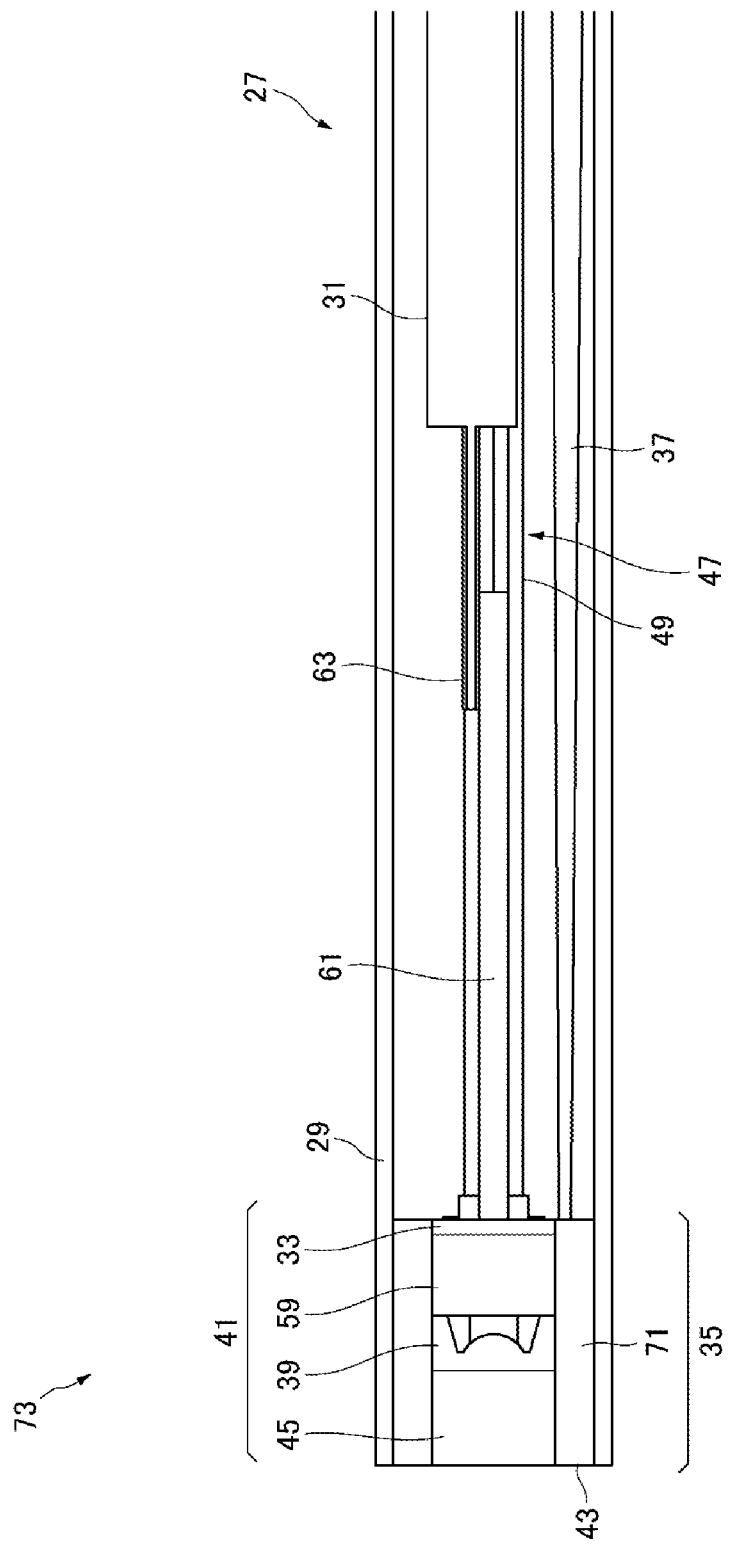
FIG. 16 is a side sectional view of the endoscope shown in FIG. 15.

FIG. 16 is a side sectional view of the endoscope 73 shown in FIG. 15. The objective cover glass 45, the lens 39, and the element cover glass 59 are embedded inside the solidified binding material 71. The back surface of the imaging element 33 fixed to the back surface of the element cover glass 59 may be exposed from the binding material 71. In this case, the conductors of the flexible wiring substrate 61 are conductively fixed to the respective pads 65 on the back surface of the imaging device 33 in the same manner as the first embodiment. The flexible wiring substrate 61 is vertically connected to the imaging element 33 in the same manner as the first embodiment. The cable 31 is connected to the rear side of the flexible wiring substrate 61.

Figure 17:
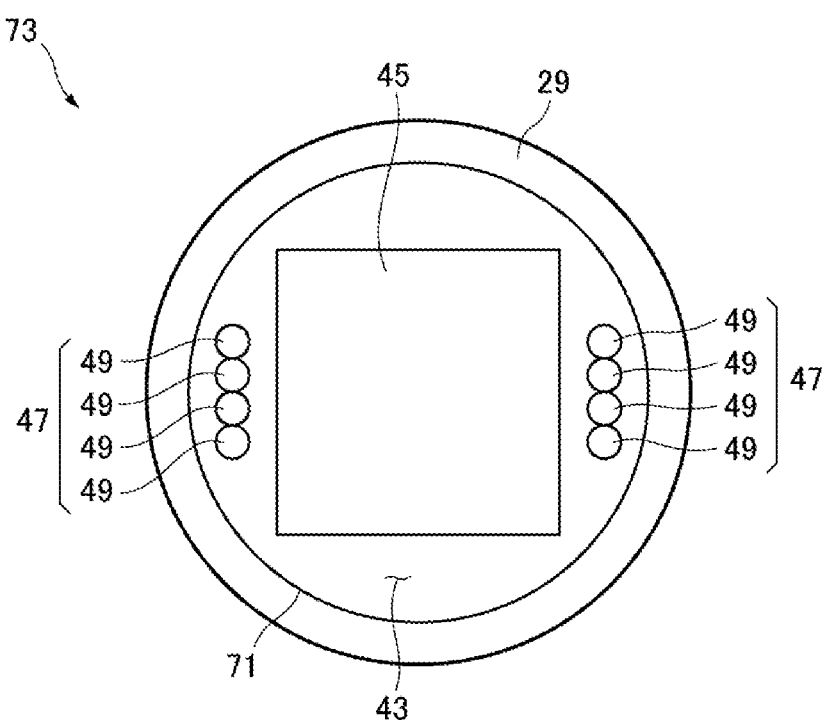
FIG. 17 is a front view of the endoscope shown in FIG. 16.

FIG. 17 is a front view of the endoscope 73 shown in FIG. 16. In the tip end surface 43 of the endoscope 73, the resin tube 29 surrounds outer circumference of the solidified binding material 71 in a cylindrical shape. The objective cover glass 45 and a pair of the light guides 47 sandwiching the objective cover glass 45 in a left-right direction are disposed on the tip end surface 43 of the binding material 71.

Figure 18:
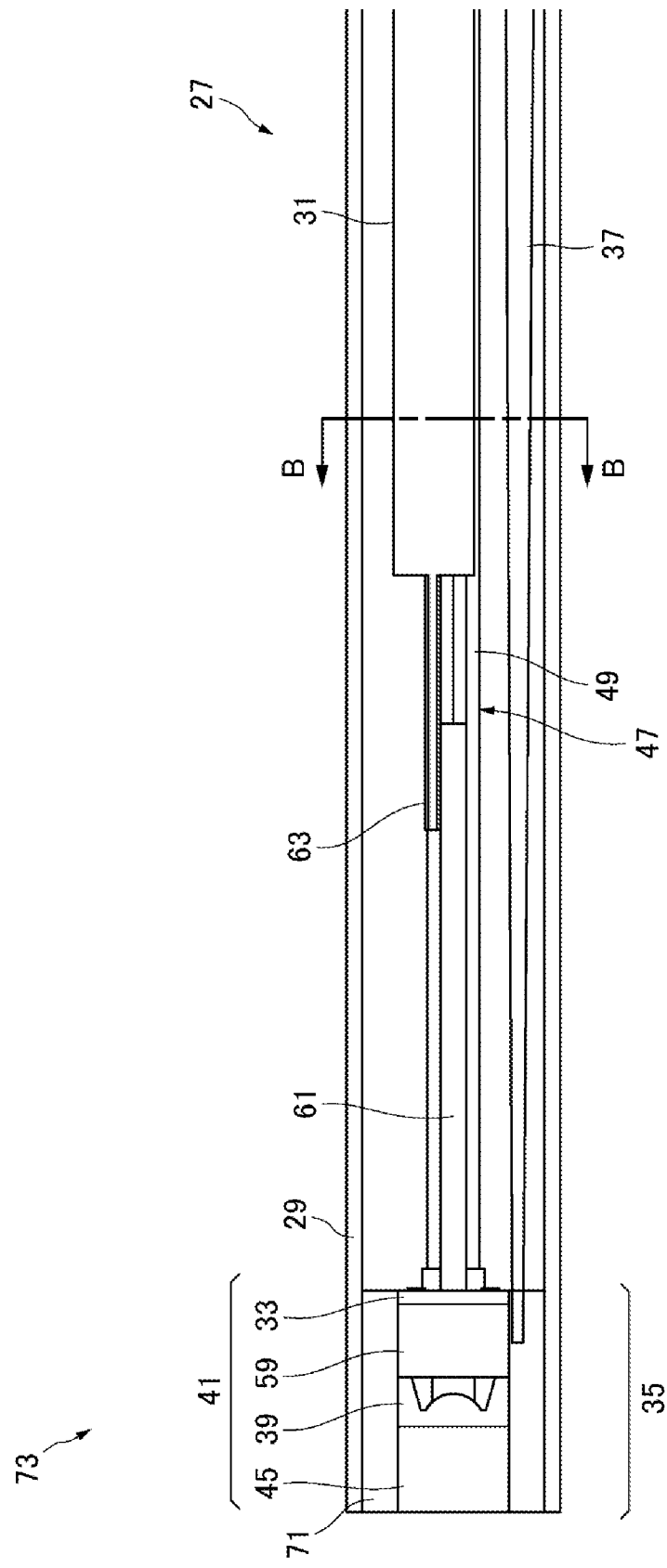
FIG. 18 is a side sectional view of an endoscope of seeing through a binding material into which a tip end of an elastic wire is embedded.

FIG. 18 is a side sectional view of the endoscope 73 of seeing through the binding material 71 in which the tip end of the elastic wire 37 is embedded. In the endoscope 73, the tip end of the elastic wire 37 embedded in the binding material 71 extends closer to the tip end surface 43 than the imaging element 33.

Figure 19:
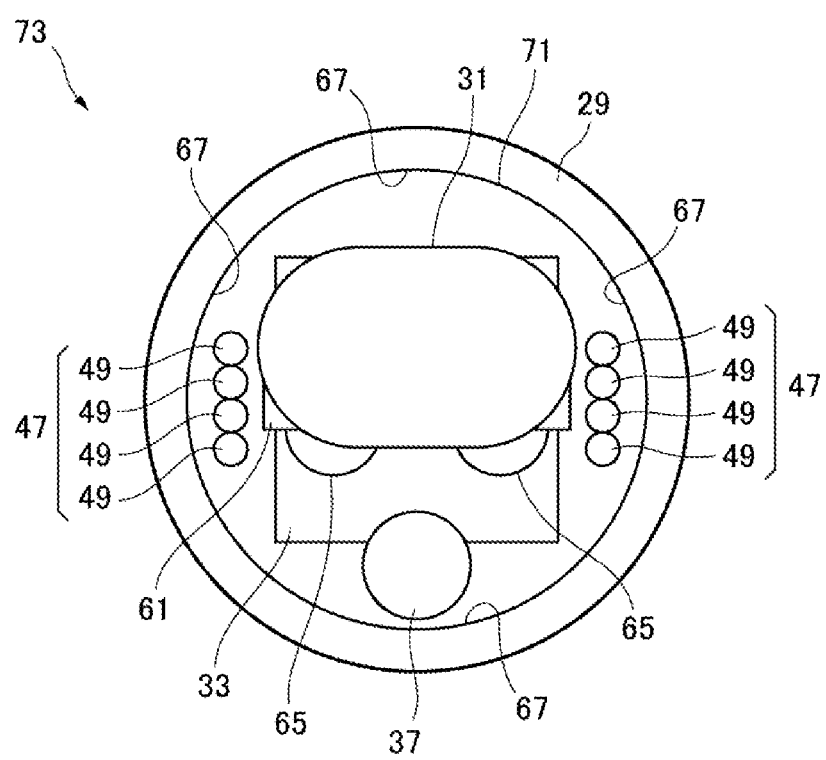
FIG. 19 is a sectional view taken along B-B of FIG. 18.

FIG. 19 is sectional view taken along B-B of FIG. 18. Also, in the endoscope 73, the elastic wire 37 is disposed outside the imaging element 33. In FIG. 19, a part of the outer shape of the elastic wire 37 overlaps the imaging element 33, and this is because the section of the large-diameter portion elastic wire 37 shown in FIG. 18 is viewed from the back. Substantially, in the elastic wire 37, as shown in FIG. 18, a small-diameter tip end side of the tapered shape is embedded and fixed into the binding material 71 outside the imaging element 33.

Next, working of a configuration of the endoscope 73 according to the second embodiment will be described.

In the endoscope 73, the tip end of the elastic wire 37 having predetermined flexural rigidity is embedded ang fixed into the binding material 71 and is inserted through the resin tube 29 to the proximal side. Therefore, even if the endoscope 73 has a proximal side and is inserted into a blood vessel or the like, a pushing force is transmitted to the tip end holder 35 by the predetermined flexural rigidity. As a result, even if the endoscope 73 has a small outer diameter of 1 mm or less, it is sure to obtain good pushability where buckling is reduced with respect to the tip end holder 35 of 1.5 m in front.

In the endoscope 73, the resin tube 29 extends to the tip end surface 43 of the tip end holder 35, the resin tube 29 of the tip end holder 35 is filled with the binding material 71, and the imaging unit 41 and the tip end of the elastic wire 37 are embedded and fixed into the binding material 71.

In the endoscope 73, the resin tube 29 for housing the imaging element 33 is circular. In a structure in which the imaging element 33 is housed at a maximum size in an inner circumferential circle of the resin tube 29, four spaces 67 are generated between the inner circumferential circles of the imaging element 33 and the resin tube 29. As described above, each side of the square of the imaging element 33 is a chord, and the space 67 is a crescent shape surrounded by the chord and an arc of the resin tube 29.

The endoscope 73 is mainly filled with the binding material 71 in the four spaces 67. The tip end of the elastic wire 37 is embedded and fixed into the binding material 71 filled in any one of the spaces 67. Therefore, the elastic wire 37 can be routed along the cable 31, and interference with the cable 31 can be avoided. Accordingly, the endoscope 73 can easily fix the elastic wire 37 by effectively using the binding material 71 for fixing the imaging unit 41 while reducing the diameter by effectively using the excess spaces within the limited circular section. That is, the endoscope 73 achieves both pushability and reduction in diameter.

In the endoscope 73, the tip end of the elastic wire 37 extends closer to the tip end surface 43 than the imaging element 33.

Figure 20:
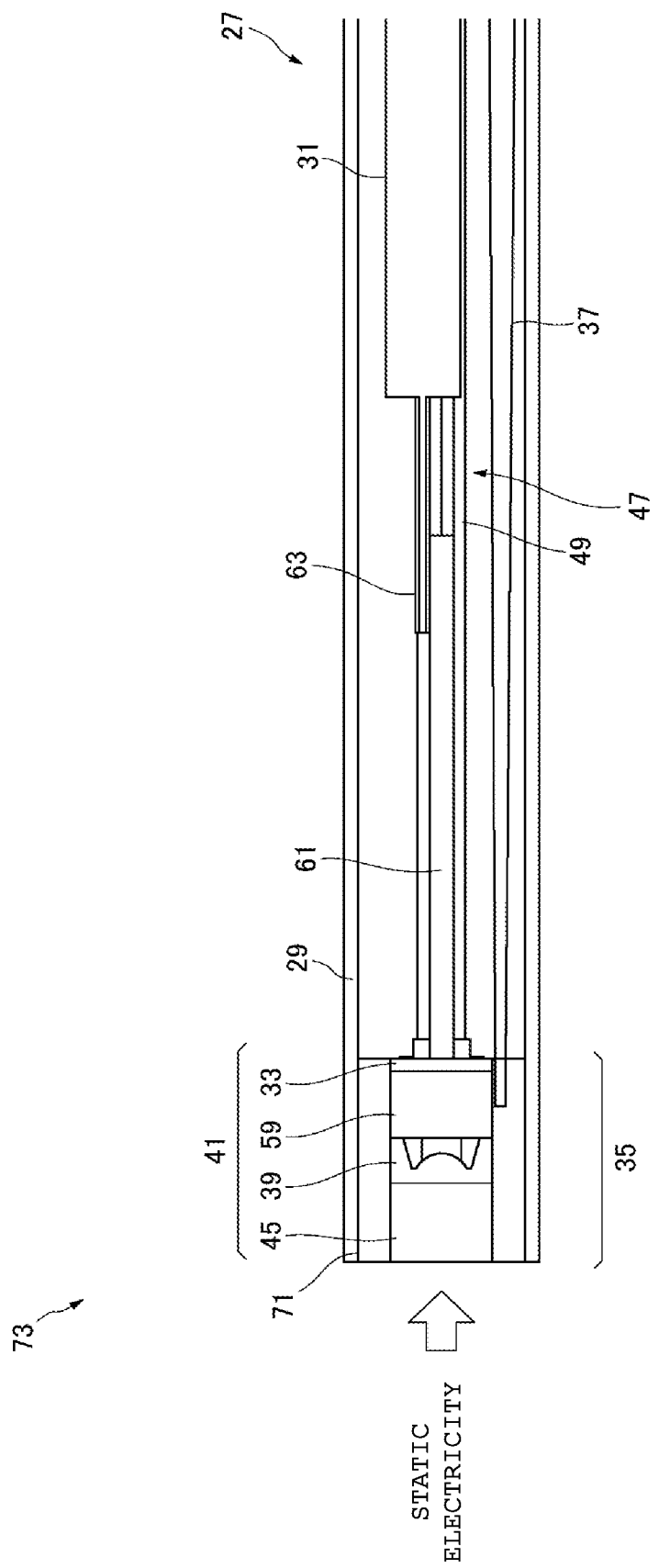
FIG. 20 is a working explanatory diagram of the endoscope according to the second embodiment.

FIG. 20 is a working explanatory diagram of the endoscope 73 according to the second embodiment. In the endoscope 73, the tip end of the elastic wire 37 is disposed closer to the tip end surface 43 than the imaging element 33. Therefore, a breakdown voltage from the tip end surface 43 to the tip end of the elastic wire 37 can be made smaller than a breakdown voltage from the tip end surface 43 to the imaging element 33. Due to a difference in the breakdown voltage, static electricity applied to the tip end surface 43 is discharged to the tip end of the elastic wire 37 while flowing into the imaging element 33 is reduced. That is, by installing the elastic wire 37 for inducing static electricity between a static electricity applied portion and the imaging element 33, static electricity can be reliably released to the arc portion via the elastic wire 37 and the plug 19, and the imaging element 33 can be precisely protected. In the endoscope 73, the elastic wire 37 is extended to the tip end surface side than the imaging element 33, and the structure is extremely simple. As a result, the diameter is easily reduced as compared with the structure in which the bottomed cylindrical portion 51 is provided.

Third Embodiment

Next, an example of an endoscope 75 according to the third embodiment will be described.

Figure 21:
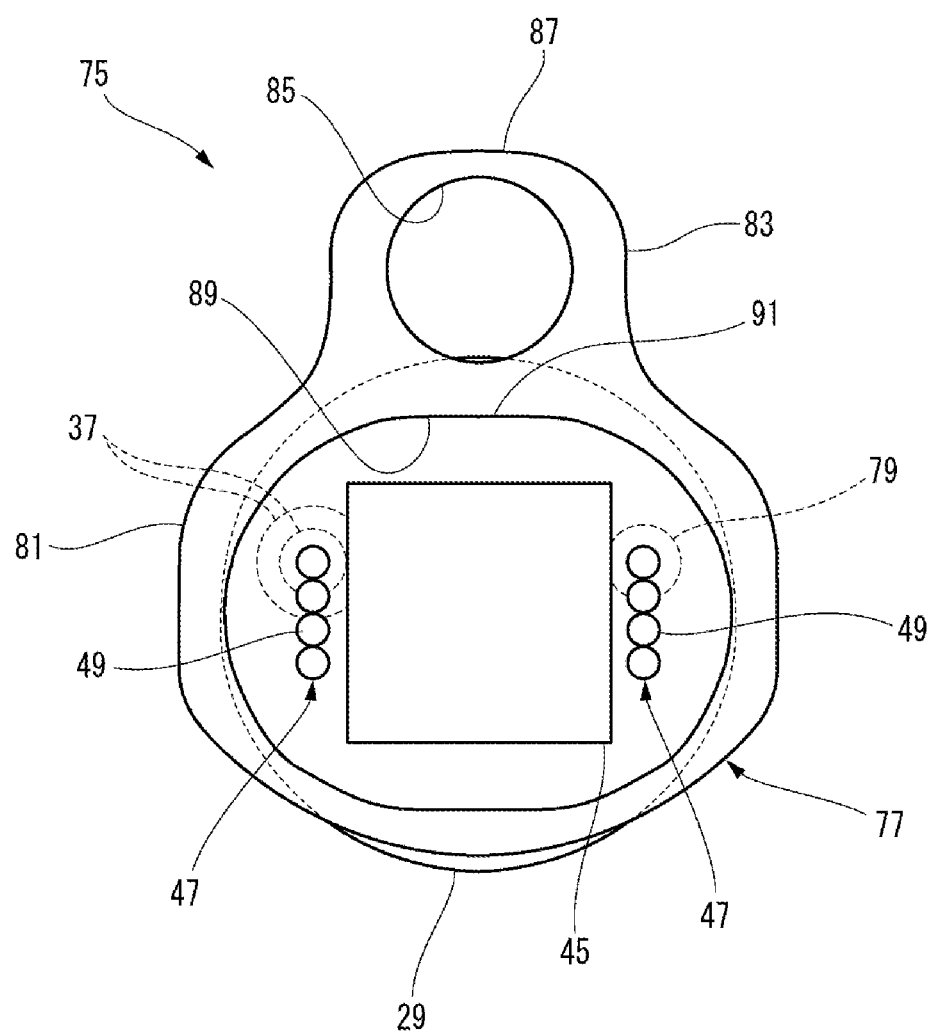
FIG. 21 is a front view of an endoscope according to a third embodiment.

FIG. 21 is a front view of the endoscope according to the third embodiment. In the third embodiment, the same components as the components shown in the first embodiment are denoted by the same reference signs, and repeated description thereof is omitted.

The endoscope 75 according to the third embodiment includes a lens 39 provided at a tip end in a direction of insertion into a body to be examined and on which imaging light is incident and, an imaging element 33 provided at a rear end of the lens 39 and on which imaging light is imaged, a conductive member (for example, a tip end holder 77) that covers the lens 39 and the imaging element 33, and an elastic wire 37 having flexibility and flexural rigidity with a tip end disposed outside the imaging element 33, which is inserted through the resin tube 29 and extends, and a grounding member (SUS wire 79) for grounding the conductive member 77.

The endoscope 75 differs from the endoscope 11 according to the first embodiment in that a shape of the tip end holder 77 is different and the endoscope 75 has the SUS wire 79 that is a grounding member.

The tip end holder 77 has a projecting portion 83 on an upper side of a flat cylindrical portion 81 having a generally elliptical section having a long axis in a left-right direction. The projecting portion 83 includes a guide wire hole 85 for passing a guide wire (not shown). The guide wire hole 85 is formed in the projecting portion 83 by leaving a bridge portion 87 at the top. A thickness of the bridge portion 87 (that is, a thickness in the vertical direction) is set to, for example, 50 μm.

The tip end holder 77 has only two holes on the tip end face: the guide wire hole 85 and an observation hole 89 in which the objective cover glass 45 and the optical fiber 49 are disposed. The objective cover glass 45 and the optical fiber 49 disposed inside the observation hole 89 are stably fixed by a black resin 91 filled in the observation hole 89.

The tip end holder 77 has the mounting tube 55 protruding rearward from a rear end of the flat cylindrical portion 81. The resin tube 29 is fitted and connected to the outer circumference of the mounting tube 55. In the tip end holder 77, the flat cylindrical portion 81, the projecting portion 83, and the mounting tube 55 are integrally formed of metal. As the metal, for example, SUS (stainless steel) can be used. The resin tube 29 is formed to have a thickness of, for example, 75 μm. The resin tube 29 is connected to the mounting tube 55 extending from the rear end portion of the tip end holder 77, and the cable 31, the optical fiber 49, the elastic wire 37, the SUS wire 79, and the like conductively connected to the imaging element 33 are inserted through the inside. The mounting tube 55 has a substantially elliptical sectional shape that is orthogonal to the axis.

Figure 22:
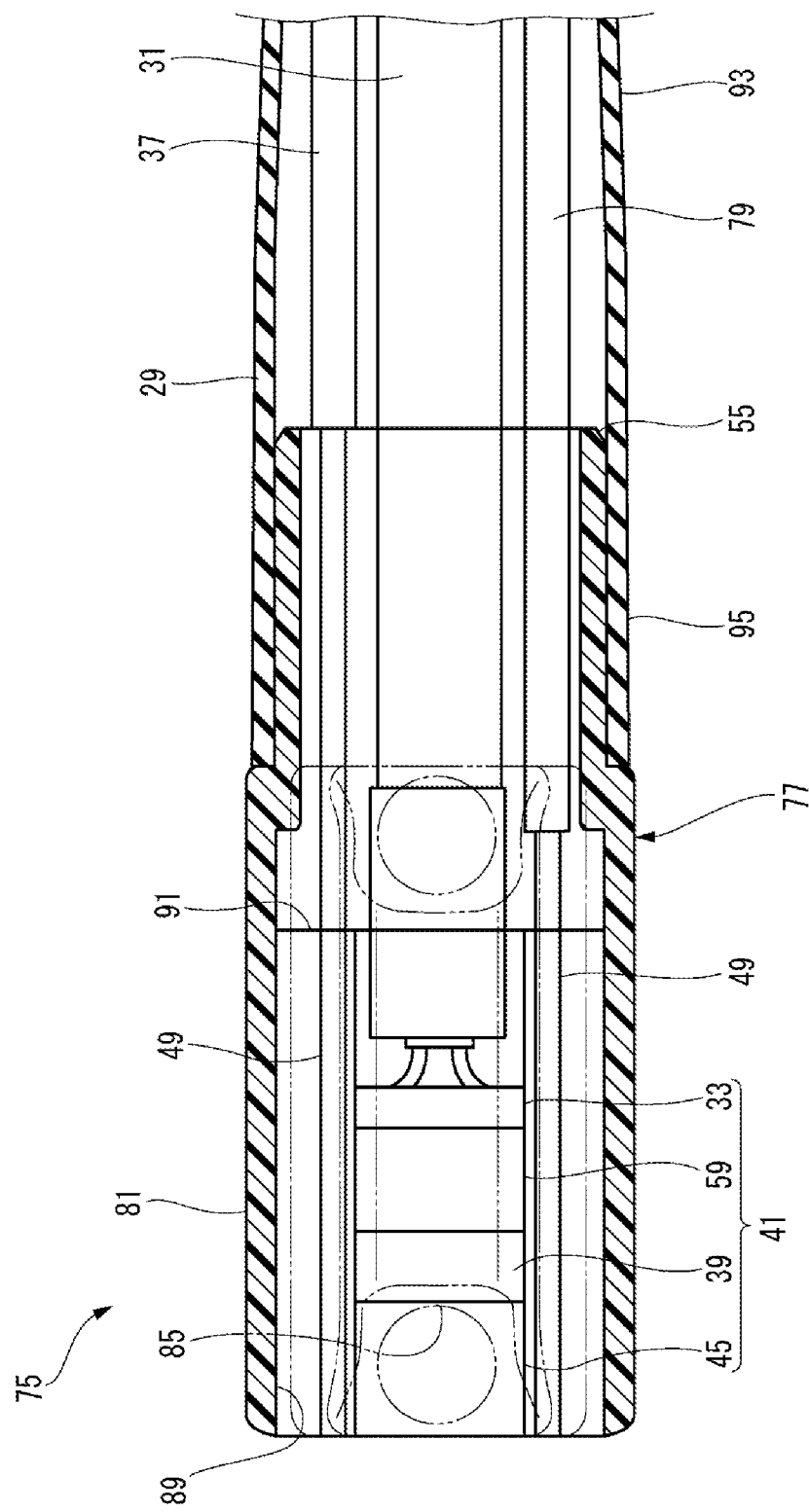
FIG. 22 is a plan view of a tip end portion of the endoscope shown in FIG. 21.

FIG. 22 is a plan view of seeing through the tip end portion of the endoscope 75 shown in FIG. 21. Most of the entire length of the insertion portion 17 is covered with the resin tube 29. The resin tube 29 is formed into a tubular shape with, for example, a resin material having flexibility. The resin tube 29 can include a single wire, a plurality of wires, and a braid of tensile strength wires on the inner circumferential side for the purpose of, for example, imparting strength. Examples of the tensile strength wire include an aramid fiber such as a poly-p-phenylene terephthalamide fiber, polyester fibers such as a polyarylate fiber, a poly para-phenylene benzobisoxazole fiber, and a polyethylene terephthalate fiber, and a thin wire of nylon fiber and tungsten or a thin wire of stainless steel. The resin tube 29 is a perfect circular portion 93 whose sectional shape orthogonal to the axis is a perfect circle, but is a flat portion 95 having a substantially elliptical sectional shape by being deformed and fitted into the mounting tube 55 since the resin tube 29 has flexibility.

The elastic wire 37 is disposed on the left side in the front view of the tip end holder 77 shown in FIG. 21. The tip end of the elastic wire 37 is disposed close to the rear end surface of the mounting tube 55. The tip end surface of the elastic wire 37 is disposed in contact with or slightly away from the rear end surface of the mounting tube 55. Since the elastic wire 37 made of Ni—Ti is disposed in contact with the tip end holder 77, it is possible to omit welding with high difficulty in fixing to the tip end holder 77 made of SUS of a dissimilar metal. It is needless to say that the elastic wire 37 may be fixed to the mounting tube 55. Since the elastic wire 37 is disposed in contact with or close to the rear end surface of the mounting tube 55 of the tip end holder 77, an axial force from the elastic wire 37 is transmitted to the tip end holder 77 without loss even if the elastic wire 37 is not fixed.

Also, in the third embodiment, as described above, the elastic wire 37 may be formed to have different flexibility between the tip end side of the elastic wire 37 and the base end side of the elastic wire 37. That is, the elastic wire 37 has a taper shape that is tapered toward the tip end side, so that the tip end side may be formed more flexible than the base end side. A length of the tapered shape portion can be set to, for example, about 200 mm rearward of the tip end holder 77. Accordingly, as described above, in the endoscope 75, while the pushability is ensured, bending followability of the tip end side of the elastic wire 37 at the time of insertion into the bent body cavity can be enhanced, and insertability of a bending portion can be improved.

Figure 23:
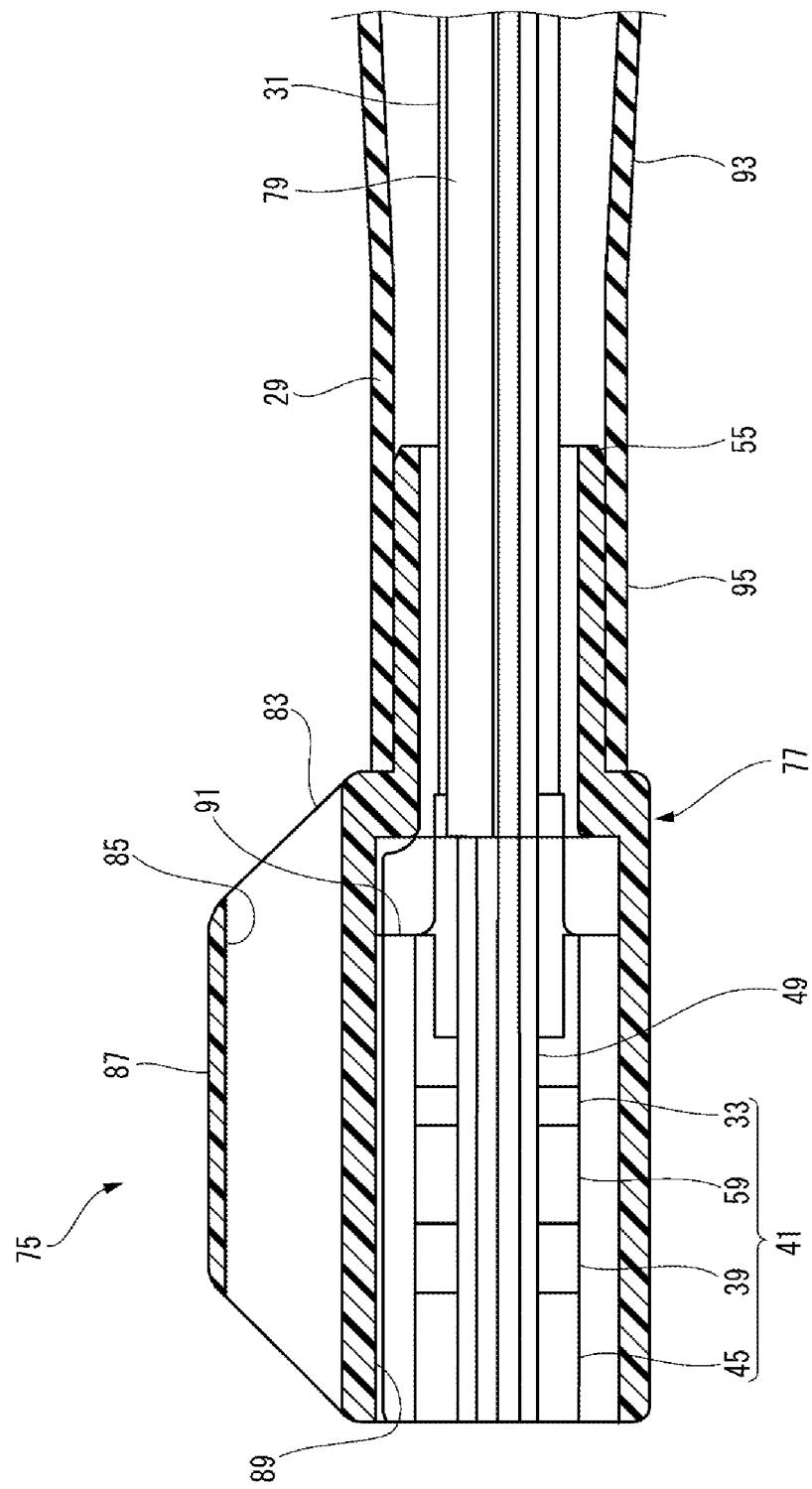
FIG. 23 is a side view of FIG. 22.

FIG. 23 is a side view of FIG. 22. The SUS wire 79 is inserted into the tip end holder 77 from the rear end side of the mounting tube 55 and is conductively fixed to an inner surface of the mounting tube 55 or the flat cylindrical portion 81. The SUS wire 79 is inserted through the mounting tube 55, for example, the tip end thereof is conductively fixed to the inner circumferential surface of the rear end portion of the flat cylindrical portion 81. The conductive fixing is performed by welding, brazing, or the like. The SUS wire 79 is formed by twisting 7 to 14 wires having an outer diameter of about 60 m. Since the tip end holder 77 and the SUS wire 79 have the same material, easy and reliable conductive fixing is possible. A commercial product of the SUS wire 79 can be obtained at a low price.

Next, working of a configuration of the endoscope 75 according to the third embodiment will be described.

The endoscope 75 can be used by being inserted into a guide catheter (not shown) inserted to house the guide wire after the guide wire is inserted into a body to be examined (for example, a human body), for example, at the time of operation or examination. The guide catheter is inserted through, for example, a blood vessel in the body to be examined. As a specific dimension example, the guide catheter has an outer diameter of, for example, 1.8 mm and an inner diameter of 1.5 mm. The guide wire is threaded through the guide catheter. The guide wire has an outer diameter of, for example, 0.35 mm. The endoscope 75 is threaded through the guide catheter together with the guide wire. Therefore, the endoscope 75 includes the guide wire hole 85 for passing the guide wire. Since the endoscope 75 is threaded through the guide catheter by providing the guide wire hole 85, a maximum outer diameter is set to, for example, 1.35 mm or less.

By providing the elastic wire 37, even if the endoscope 75 has a proximal end side and is inserted into a blood vessel or the like, a pushing force is transmitted to the tip end holder 77 by the predetermined flexural rigidity similarly to the above working effect. As a result, even if the endoscope 75 has a small outer diameter of 1 mm or less, it is sure to obtain good pushability where buckling is reduced with respect to the tip end holder 77 of 1.5 m in front.

In the endoscope 75, the tip end holder 77 is made of metal that covers the imaging unit 41 and formed. The SUS wire 79 is conductively connected to the tip end holder 77. The SUS wire 79 is inserted through the inside of the resin tube 29 and is conductively connected to the arc portion in the video processor 15 via the plug 19. Accordingly, the imaging unit 41 housed inside the tip end holder 77 can be reliably shielded (namely electromagnetic shielding) against static electricity flying from a 3600 direction around the axis. As a result, the endoscope 75 can improve operational reliability of the imaging unit 41 while realizing reduction in diameter.

Since the endoscope 75 has both the elastic wire 37 and the SUS wire 79, it is possible to realize pushability, good productivity, and operational reliability together. That is, when Ni—Ti is used for the elastic wire 37, good pushability due to superelasticity is obtained, but fixing is difficult due to welding with the tip end holder 77 made of SUS. On the other hand, if a stainless steel wire is used for the elastic wire 37, welding with the tip end holder 77 becomes easy, but good pushability is difficult to be obtained. Therefore, according to the endoscope 75, by using the cheap and small-diameter SUS wire 79, good pushability using Ni—Ti for the elastic wire 37 can be obtained, and easy welding with the tip end holder 77 by the SUS wire 79 can be realized. As a result, mass productivity of the endoscope 75 having high reliability can be enhanced.

Although the tip end holder 77 described in the third embodiment has been described as having the guide wire hole 85, it is needless to say that the endoscope 75 may not have the projecting portion 83 or the guide wire hole 85 in the tip end holder 77. In this case, the endoscope 75 is configured to include the elastic wire 37 and the SUS wire 79 with respect to the general tip end holder shown in the first embodiment.

Therefore, according to the endoscope 11, the endoscope 69, the endoscope 73, and the endoscope 75 according to the respective embodiments, it is possible to achieve both pushability for reducing buckling of the tip end side of the insertion portion and reduction in diameter of the tip end side of the insertion portion.

Although various embodiments are described above with reference to the drawings, it is needless to say that the present disclosure is not limited to such examples. It will be apparent to those skilled in the art that various alterations, modifications, substitutions, additions, deletions, and equivalents can be conceived within the scope of the claims, and it should be understood that they also naturally belong to the technical scope of the present disclosure. Each constituent element in the various embodiments described above may be combined optionally in a range out deviating from the spirit of the invention.

The present application is based on Japanese Patent Application No. 2018-084435 filed on Apr. 25, 2018, the contents of which are incorporated herein by reference.

INDUSTRIAL APPLICABILITY

The present disclosure is useful as an endoscope that achieves both pushability for reducing buckling of the tip end side of the insertion portion and reduction in diameter of the tip end side of the insertion portion.

REFERENCE SIGN LIST

11 Endoscope
29 Resin tube
31 Cable
33 Imaging element
35 Tip end holder
37 Elastic wire
39 Lens
41 Imaging unit
43 Tip end surface
51 Bottomed cylindrical portion
53 Axial line
71 Binding material

The invention claimed is:

1. An endoscope having a proximal end and a distal end and comprising:
   an imaging unit that has a lens and an imaging element;
   a tip end holder at the distal end and which houses the imaging unit,
   a resin tube that proximally extends from inside the tip end holder to the proximal end, and that accommodates a cable which is conductively connected to the imaging element therein; and
   an elastic wire having flexibility and flexural rigidity, and further having an elastic wire tip end disposed outside the imaging element, the elastic wire proximally extending through and along the resin tube from the tip end holder to the proximal end, wherein:
   a portion of the resin tube disposed inside the tip end holder is filled with a binding material, and
   the imaging unit and the elastic wire tip end are embedded and fixed in the binding material.

2. The endoscope according to claim 1, wherein
the tip end holder has a bottomed cylindrical portion made of metal that houses the imaging unit therein, and
the tip end of the elastic wire is conductively connected to the bottomed cylindrical portion.

3. The endoscope according to claim 2, wherein
a position of the elastic wire tip end is closer to the distal end than a position of the imaging element.

4. The endoscope according to claim 1, wherein
the elastic wire tip end has higher flexibility than a base end of the elastic wire.

5. The endoscope according to claim 1, wherein
the elastic wire is formed using a shape memory alloy.

* * * * *